(12) United States Patent
Cho et al.

(10) Patent No.: US 11,246,494 B2
(45) Date of Patent: Feb. 15, 2022

(54) ELECTRONIC DEVICE AND METHOD OF OPERATING THE SAME

(71) Applicant: Samsung Electronics Co., Ltd., Gyeonggi-do (KR)

(72) Inventors: Minhyun Cho, Gyeonggi-do (KR); Taehyeon Kim, Gyeonggi-do (KR); Seunghyun Lee, Gyeonggi-do (KR); Jeongsu Lee, Gyeonggi-do (KR); Daehyeong Lim, Gyeonggi-do (KR); Daniel Joe, Gyeonggi-do (KR); Seongmin Je, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 105 days.

(21) Appl. No.: 16/701,740

(22) Filed: Dec. 3, 2019

(65) Prior Publication Data
US 2020/0297215 A1    Sep. 24, 2020

(30) Foreign Application Priority Data

Mar. 18, 2019  (KR) .................. 10-2019-0030312

(51) Int. Cl.
  *A61B 5/00*     (2006.01)
  *A61B 5/0205*   (2006.01)
  *A61B 5/024*    (2006.01)

(52) U.S. Cl.
  CPC ............ *A61B 5/0205* (2013.01); *A61B 5/742* (2013.01); *A61B 5/7405* (2013.01);
  (Continued)

(58) Field of Classification Search
  CPC ..... A61B 5/0205; A61B 5/7475; A61B 5/742; A61B 5/7405; A61B 5/02427;
  (Continued)

(56) References Cited

U.S. PATENT DOCUMENTS

| 8,313,439 B2 | 11/2012 | McCombie et al. |
| 10,151,602 B2 | 12/2018 | Park et al. |

(Continued)

FOREIGN PATENT DOCUMENTS

| CN | 108606801 A | * 10/2018 |
| CN | 108606801 B |   3/2021 |

(Continued)

OTHER PUBLICATIONS

International Search Report dated Mar. 12, 2020.

*Primary Examiner* — Joseph M Dietrich
*Assistant Examiner* — Michael T. Holtzclaw
(74) *Attorney, Agent, or Firm* — Cha & Reiter, LLC

(57) ABSTRACT

Provided is an electronic device including a housing; a battery; a user interface; a photoplethysmogram (PPG) sensor including a light receiving module exposed through a portion of the housing, at least one light emitting diode (LED), and at least one photodiode; a processor operatively connected to the battery, the user interface, and the PPG sensor; and a memory. According to an embodiment, the memory stores instructions that, when executed, cause the processor to determine whether the PPG sensor is facing a surface of an external object having a reference color, determine whether to perform a test of the PPG sensor based on whether the PPG sensor is facing the surface, receive data from the PPG sensor by operating the PPG sensor in response to determining to perform the test, and perform calibration of the PPG sensor based on at least a portion of the received data. Other embodiments are possible.

18 Claims, 15 Drawing Sheets

(52) U.S. Cl.
CPC ........ *A61B 5/7475* (2013.01); *A61B 5/02427* (2013.01); *A61B 2560/0214* (2013.01); *A61B 2560/0223* (2013.01); *A61B 2562/0219* (2013.01)

(58) Field of Classification Search
CPC .... A61B 2560/0214; A61B 2560/0223; A61B 2562/0219; A61B 5/7207; A61B 2560/0456; A61B 2562/043; A61B 5/681; A61B 5/1118; A61B 5/1032; A61B 5/14551; A61B 2562/046; A61B 5/02416
See application file for complete search history.

(56) References Cited

U.S. PATENT DOCUMENTS

| | | |
|---|---|---|
| 10,241,042 B2 | 3/2019 | Kim |
| 2015/0057511 A1 | 2/2015 | Basu |
| 2015/0160048 A1 | 6/2015 | Schuessler |
| 2016/0302674 A1* | 10/2016 | Moyer ................ A61B 5/0002 |
| 2016/0360986 A1 | 12/2016 | Lange |
| 2017/0042485 A1 | 2/2017 | Chung et al. |
| 2017/0209055 A1* | 7/2017 | Pantelopoulos ..... A61B 5/7203 |
| 2017/0215811 A1* | 8/2017 | Newberry .............. G16H 40/63 |
| 2018/0039233 A1* | 2/2018 | Shim ...................... G04G 21/02 |
| 2018/0184920 A1* | 7/2018 | Rabinovich .......... A61B 5/0205 |
| 2018/0247713 A1* | 8/2018 | Rothman ............... G16H 50/30 |
| 2018/0368701 A1* | 12/2018 | Vule .................... A61B 5/0205 |
| 2019/0069781 A1 | 3/2019 | Kim et al. |

FOREIGN PATENT DOCUMENTS

| | | |
|---|---|---|
| KR | 10-2016-0104247 A | 9/2016 |
| KR | 10-2017-0019745 A | 2/2017 |
| KR | 10-2018-0010538 A | 1/2018 |
| KR | 10-2019-0027238 A | 3/2019 |
| KR | 10-2148252 B1 | 8/2020 |

* cited by examiner

ELECTRONIC DEVICE AND METHOD OF OPERATING THE SAME

CROSS-REFERENCE TO RELATED APPLICATION(S)

This application is based on and claims priority under 35 U.S.C. 119 to Korean Patent Application No. 10-2019-0030312, filed on Mar. 18, 2019, in the Korean Intellectual Property Office, the disclosures of which are herein incorporated by reference in their entireties.

BACKGROUND

1. Technical Field

One or more embodiments of the instant disclosure generally relate to an electronic device including a sensor and a method of operating the same.

2. Description of Related Art

Recently developed electronic devices include various sensors. In particular, electronic devices including sensors capable of measuring the user's biometric information have been developed recently. Such an electronic device may measure various pieces of biometric information of the user using sensors. For example, the electronic device may measure the user's heart rate, oxygen saturation, stress, blood pressure, and blood sugar.

However, when such a biometric sensor is damaged or has deteriorated, a problem with conventional electronic devices is that they do not notify the user of the damage and may continue to provide incorrect sensing values, thereby failing to guarantee accuracy of the sensor.

SUMMARY

According to an embodiment of the disclosure, an electronic device includes a housing; a rechargeable battery; a user interface; a photoplethysmogram (PPG) sensor including a light receiving module exposed through a portion of the housing, at least one light emitting diode (LED), and at least one photodiode; a processor operatively connected to the battery, the user interface, and the PPG sensor; and a memory operatively connected to the processor. According to an embodiment, the memory stores instructions that, when executed, cause the processor to determine whether the PPG sensor is facing a surface of an external object having a reference color, to determine whether to perform a test of the PPG sensor based on whether the PPG sensor is facing the surface, to receive data from the PPG sensor by operating the PPG sensor in response to determining to perform the test, and to perform calibration of the PPG sensor based on at least a portion of the received data.

According to an embodiment of the disclosure, a method of operating an electronic device includes determining whether a photoplethysmogram (PPG) sensor including a light receiving module exposed through a portion of a housing of the electronic device, at least one LED, and at least one photodiode facing a surface of an external object having a reference color; determining whether to perform a test of the PPG sensor based on whether the PPG sensor is facing the surface; receiving data from the PPG sensor by operating the PPG sensor in response to determining to perform the test; and performing calibration of the PPG sensor based on at least a portion of the received data.

Additional aspects will be set forth in part in the description which follows and, in part, will be apparent from the description, or may be learned by practice of the presented embodiments.

BRIEF DESCRIPTION OF THE DRAWINGS

The above and other aspects, features, and advantages of certain embodiments of the present disclosure will be more apparent from the following description taken in conjunction with the accompanying drawings, in which.

In the drawings, the same or similar reference numerals may be used for the same or similar components.

DETAILED DESCRIPTION

Certain embodiments of the instant disclosure provide an electronic device and a method of operating the same capable of testing a state of a sensor of the electronic device and calibrating sensing values to guarantee accuracy of the sensor and to provide the tested state to the user.

Figure 1:
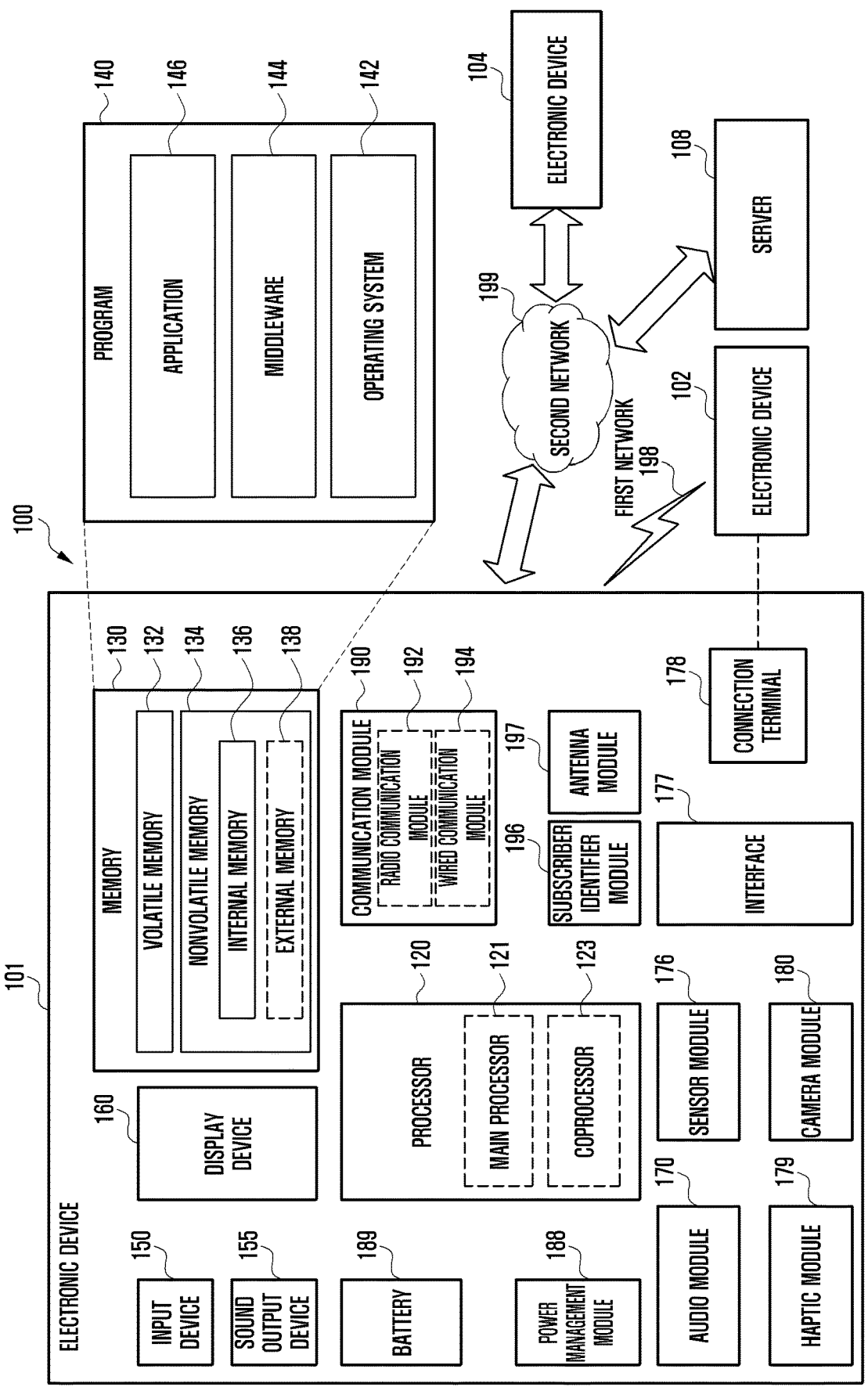
FIG. 1 is a block diagram illustrating an electronic device in a network environment according to an embodiment of the disclosure.

FIG. 1 is a block diagram illustrating an electronic device 101 in a network environment 100 according to an embodiment. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
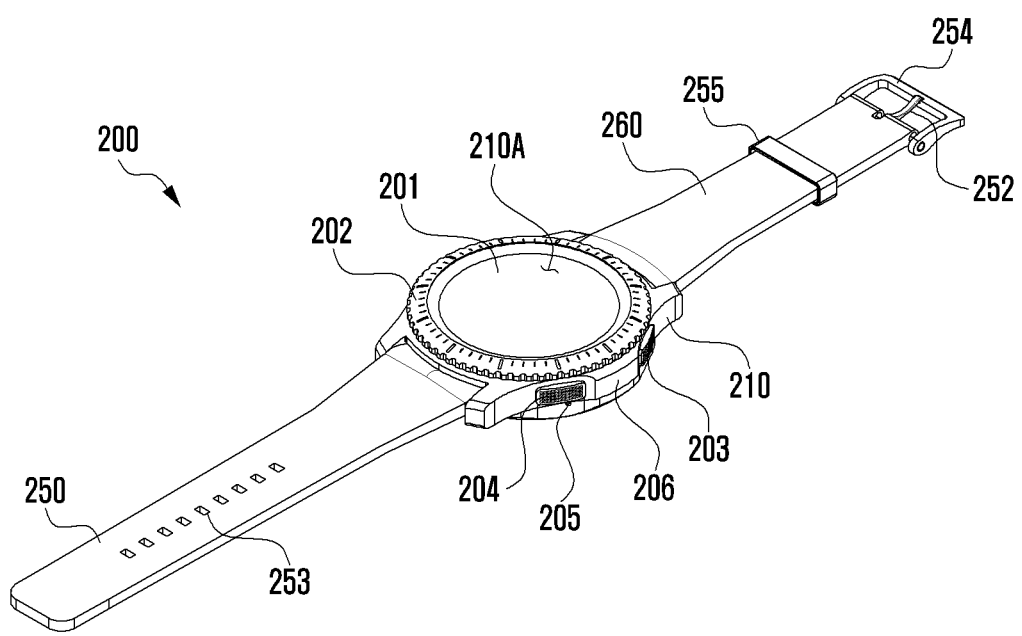
FIG. 2 is a perspective view illustrating a front surface of a mobile electronic device according to an embodiment of the disclosure.
Figure 3:
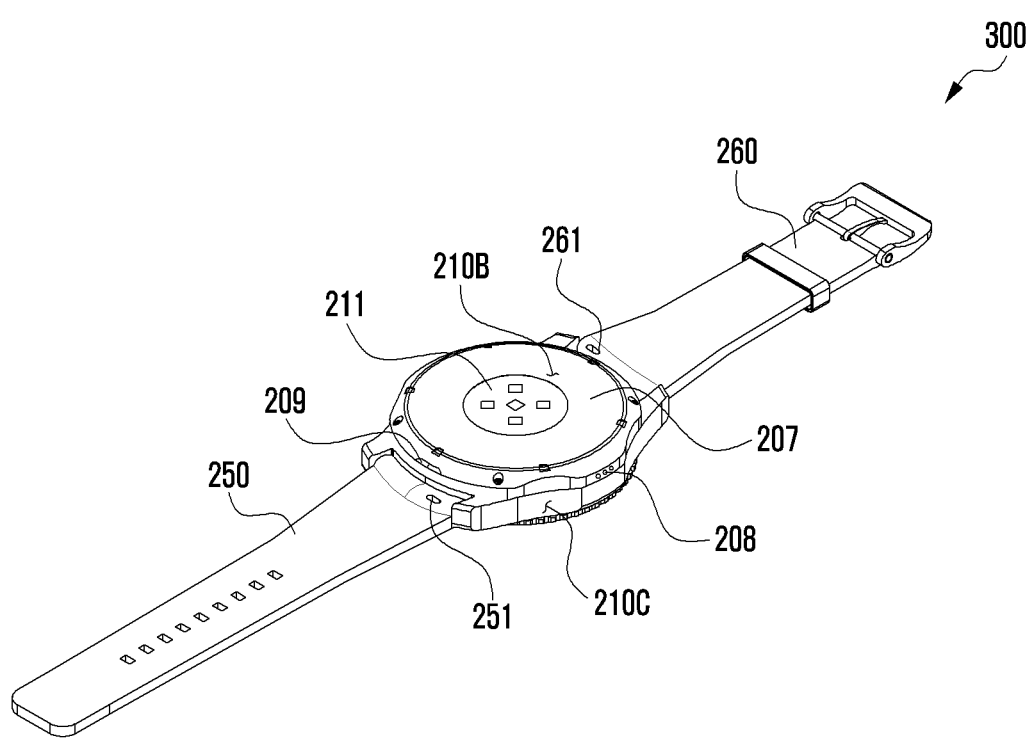
FIG. 3 is a perspective view illustrating a rear surface of the electronic device of FIG. 2 according to an embodiment of the disclosure.

FIG. 2 is a perspective view illustrating a front surface of a mobile electronic device according to an embodiment of the disclosure, and FIG. 3 is a perspective view illustrating a rear surface of the electronic device of FIG. 2 according to an embodiment of the disclosure.

With reference to FIGS. 2 and 3, an electronic device 200 (e.g., the electronic device 101 of FIG. 1), also labelled as electronic device 300 in FIG. 3, according to an embodiment may include a housing 210 including a first surface (or front surface) 210A, a second surface (or rear surface) 210B, and a side surface 210C enclosing a space between the first surface 210A and the second surface 210B; and binding members 250 and 260 connected to at least a portion of the housing 210 and configured to detachably bind the electronic device 200 to a part (e.g., wrist, ankle) of the user's body. In another embodiment (not illustrated), the housing 210 may refer to only a portion of the first surface 210A, the second surface 210B, and the side surface 210C of FIG. 2. According to an embodiment, the first surface 210A may include a front plate 201 (e.g., a polymer plate or a glass plate including various coating layers) at least partially substantially transparent. The second surface 210B may include a substantially opaque rear plate 207. The rear plate 207 may be made of, for example, coated or colored glass, ceramic, polymer, metal (e.g., aluminum, stainless steel (STS), or magnesium), or a combination of at least two of the above materials. The side surface 210C may be coupled to the front plate 201 and the rear plate 207 and include a side bezel structure (or "side member") 206 that is made of metal and/or polymer. In some embodiments, the rear plate 207 and the side bezel structure 206 may be integrally formed and be made of the same materials (e.g., metals such as aluminum). The binding members 250 and 260 may be made of various materials and be in various shapes. The binding members 250 and 260 may include an integral link and a plurality of unit links, and they may be made of woven goods, leather, rubber, urethane, metal, ceramic, or combinations of at least two of the above materials.

According to an embodiment, the electronic device 200 may include at least one of a display 220 (see FIG. 4), audio modules 205 and 208, a sensor module 211, key input devices 202, 203, and 204, and a connector hole 209. In some embodiments, the electronic device 200 may omit at least one of the components (e.g., the key input devices 202, 203, 204, connector hole 209, or sensor module 211) or may further include other components.

The display 220 may be exposed through, for example, a substantial portion of the front plate 201. The display 220 may have a shape corresponding to that of the front plate 201. Although shown here as circular, the display 220 may have various shapes such as elliptical, polygonal, etc. The display 220 may be coupled to or be disposed adjacent to a touch sensing circuit, a pressure sensor capable of measuring intensity (pressure) of a touch, and/or a fingerprint sensor.

The audio modules 205 and 208 may include a microphone hole 205 and a speaker hole 208. In the microphone hole 205, a microphone for obtaining sound from the external environment may be disposed. And, in some embodiments, a plurality of microphones may be disposed to detect the direction of the sound. The speaker hole 208 may be used to output sound from a speaker or a receiver used for phone calls. In some embodiments, the speaker hole 208 and the microphone hole 205 may be implemented into one hole or a speaker (e.g., piezo speaker) may be included without the speaker hole 208.

The sensor module 211 may generate electrical signals or data values corresponding to an operating state of the electronic device 200 or an external environment state. The sensor module 211 may include, for example, a biometric sensor module 211 (e.g., HRM sensor) disposed at the second surface 210B of the housing 210. The electronic device 200 may further include another sensor module (not illustrated), such as gesture sensor, gyro sensor, air pressure sensor, magnetic sensor, acceleration sensor, grip sensor, color sensor, infrared (IR) sensor, biometric sensor, temperature sensor, humidity sensor, illuminance sensor, etc.

The key input devices 202, 203, and 204 may include a wheel key 202 disposed at the first surface 210A of the housing 210 and that can rotate in at least one direction and/or side key buttons 203 and 204 disposed at the side surface 210C of the housing 210. The wheel key 202 may have a shape corresponding to that of the front plate 201. In another embodiment, the electronic device 200 may not include some or all of the above-mentioned key input devices 202, 203, and 204 and the non-included key input devices 202, 203, and 204 may be implemented into other forms such as soft keys on the display 220. The connector hole 209 may receive a connector (e.g., USB connector) for transmitting and receiving power and/or data to and from an external electronic device, and the electronic device may include another connector hole (not illustrated) that may receive a connector for transmitting and receiving audio signals to and from the external electronic device. In one embodiment, the electronic device 200 may further include a connector cover (not illustrated) that covers at least a portion of the connector hole 209 and that blocks inflow of foreign material into the connector hole.

The binding members 250 and 260 may be detachably bound to at least a partial area of the housing 210 using locking members 251 and 261. The binding members 250 and 260 may include one or more of a fixing member 252, fixing member fastening holes 253, band guide member 254, and band fixing ring 255.

The fixing member 252 may be configured to fix the housing 210 and the binding members 250 and 260 to a part (e.g., wrist, ankle) of the user's body. The fixing member fastening holes 253 may fix the housing 210 and the binding members 250 and 260 to the part of the user's body when the fixing member 252 is inserted into one of the fixing member fastening holes 253. When the fixing member 252 is fastened to one of the fixing member fastening holes 253, the band guide member 254 is configured to limit the range of movement of the fixing member 252. Thus, the binding members 250 and 260 may fasten the housing 210 to the user's body. The band fixing ring 255 may limit the range of movement of the binding members 250 and 260 when the fixing member 252 is inserted into one of the fixing member fastening holes 253.

Figure 4:
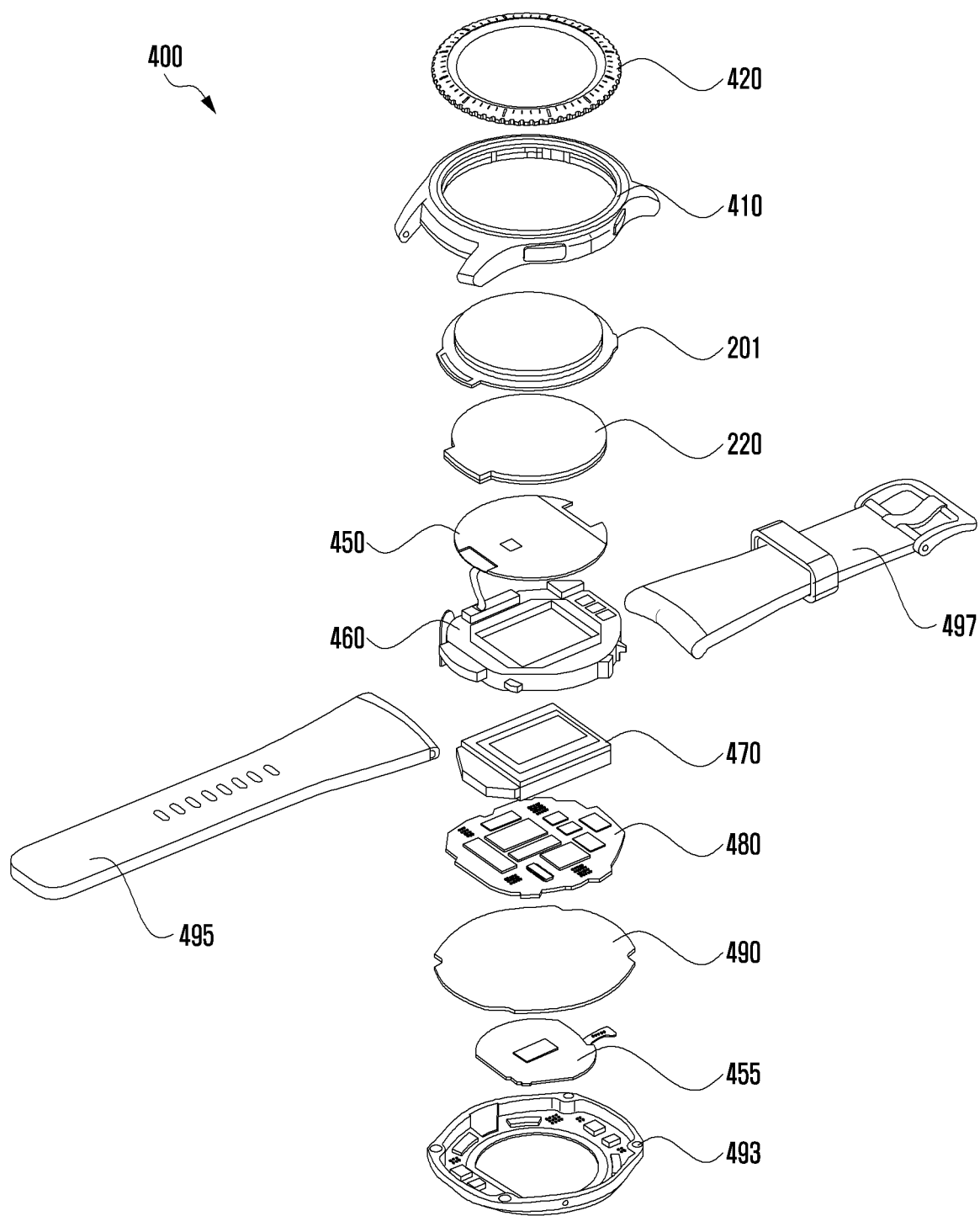
FIG. 4 is an exploded perspective view illustrating the electronic device of FIG. 2 according to an embodiment of the disclosure.

FIG. 4 is an exploded perspective view illustrating the electronic device of FIG. 2 according to an embodiment of the disclosure.

With reference to FIG. 4, an electronic device 400 may include a side bezel structure 410, wheel key 420, front plate 201, display 220, first antenna 450, second antenna 455, support member 460 (e.g., bracket), battery 470, printed circuit board 480, sealing member 490, rear plate 493, and binding members 495 and 497. Some of the components of the electronic device 400 may be the same as or similar to the corresponding components of the electronic device 200 of FIG. 2 or 3, and repeated descriptions thereof will be omitted. The support member 460 may be disposed inside the electronic device 400 to be connected to the side bezel structure 410 or may be integrally formed with the side bezel structure 410. The support member 460 may be made of, for example, metal and/or nonmetal (e.g., polymer). The display 220 may be coupled to one surface of the support member 460, and the printed circuit board 480 may be coupled to the other surface thereof. Processor, memory, and/or an interface may be mounted in the printed circuit board 480. The processor may be, for example, a central processing unit, application processor, graphic processing unit (GPU), sensor processor, and/or communication processor. Further, the processor may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Certain of the functions and steps provided in the Figures may be implemented in hardware, software or a combination of both and may be performed in whole or in part within the programmed instructions of a computer. No claim element herein is to be construed under the provisions of 35 U.S.C. § 112(f), unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

The memory may include, for example, volatile memory or nonvolatile memory. The interface may include, for example, high definition multimedia interface (HDMI), universal serial bus (USB) interface, secure digital (SD) card interface, and/or audio interface. The interface may be used to, for example, electrically or physically connect the electronic device 400 to an external electronic device, and may include a USB connector, an SD card/multi-media card (MMC) connector, or an audio connector.

The battery 470 is a device for supplying power to at least one component of the electronic device 400 and may be, for example, a non-rechargeable primary cell, a rechargeable secondary cell, or a fuel cell. At least a portion of the battery 470 may be disposed on substantially the same plane as that of, for example, the printed circuit board 480. The battery 470 may be integrally disposed inside the electronic device 400 or may be detachably disposed in the electronic device 400, meaning the battery may be removable by the user.

The first antenna 450 may be disposed between the display 220 and the support member 460. The first antenna 450 may include, for example, a near field communication (NFC) antenna, wireless charging antenna, and/or magnetic secure transmission (MST) antenna. For example, the first antenna 450 may perform short-range communication with an external device, wirelessly transmit and receive power required for charging, and transmit a short-range communication signal or a magnetic-based signal including payment data. In other embodiments, the antenna structure may be formed by some or a combination of the side bezel structure 410 and/or the support member 460.

The second antenna 455 may be disposed between the printed circuit board 480 and the rear plate 493. The second antenna 455 may include, for example, a near field communication (NFC) antenna, a wireless charging antenna, and/or a magnetic secure transmission (MST) antenna. For example, the second antenna 455 may perform short-range communication with an external device, wirelessly transmit and receive power required for charging, and transmit a near-field communication signal or a magnetic-based signal including payment data. In other embodiments, the antenna structure may be formed by some or a combination of the side bezel structure 410 and/or the rear plate 493.

The sealing member 490 may be located between the side bezel structure 410 and the rear plate 493. The sealing member 490 may be configured to block moisture and foreign materials from being introduced from the outside into the space enclosed by the side bezel structure 410 and the rear plate 493.

Figure 5:
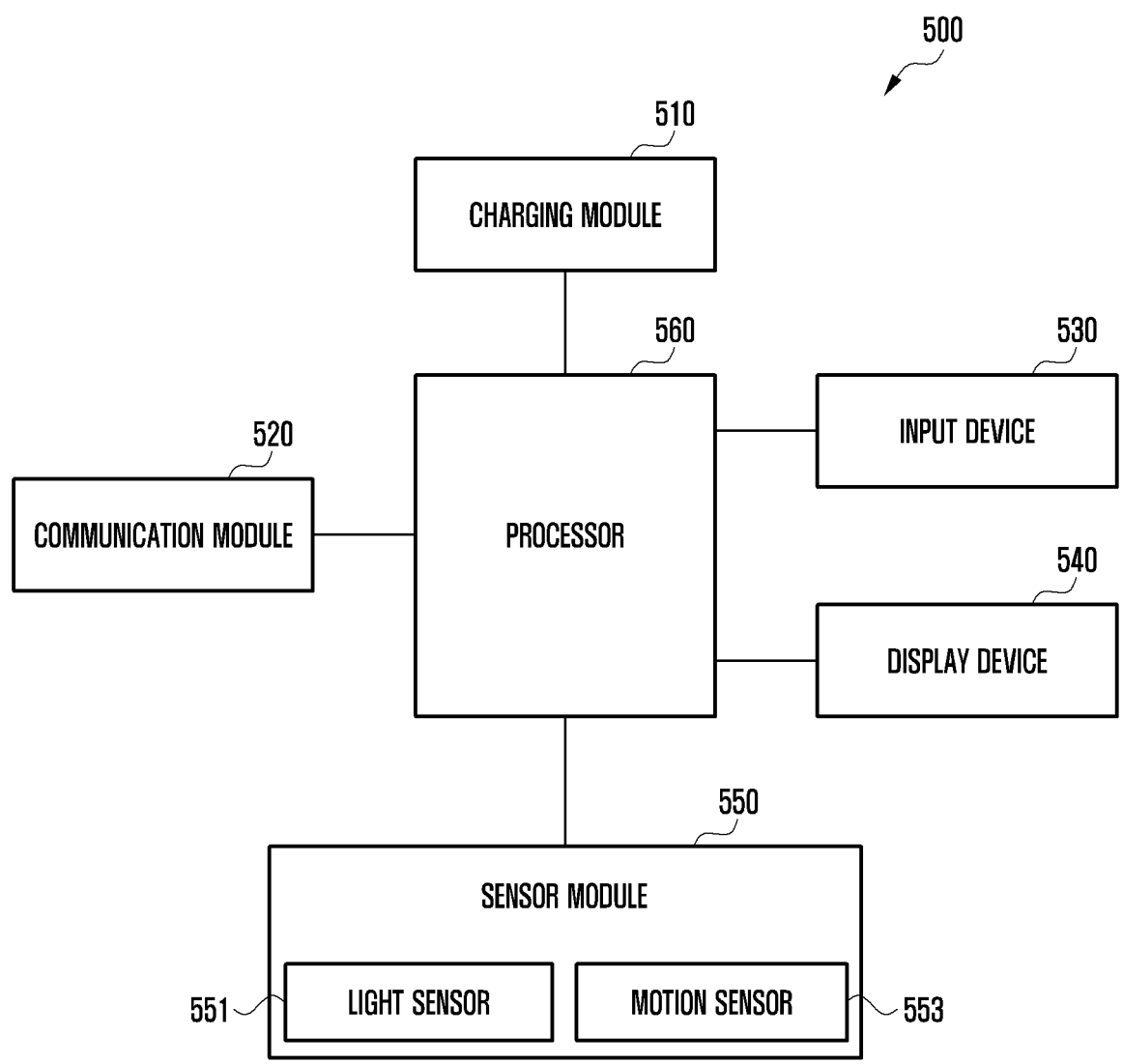
FIG. 5 is a block diagram illustrating an electronic device according to an embodiment of the disclosure.

FIG. 5 is a block diagram illustrating an electronic device 500 (e.g., the electronic device 101 of FIG. 1, the electronic device 200 of FIGS. 2 and 3, and the electronic device 400 of FIG. 4) according to an embodiment of the disclosure.

According to an embodiment of the disclosure, the electronic device may include a charging module 510, communication module 520, input device 530, display device 540, sensor module 550, and processor 560.

According to an embodiment, the charging module 510 may control charging of a battery (e.g., the battery 189 of FIG. 1 or the battery 470 of FIG. 4) of the electronic device. According to an embodiment, the charging module 510 may charge the battery either via a wire or wirelessly. According to an embodiment, the charging module 510 may recognize whether the electronic device (e.g., battery) is being charged to provide information to the processor 560. According to an embodiment, the charging module 510 may include the power management module 188 of FIG. 1.

According to an embodiment, the communication module 520 may communicate with external devices. For example, the communication module 520 may transmit and receive data or signals to or from an external device by wired or wireless means. According to an embodiment, the communication module 520 may include the communication module 190 or the antenna module 197 of FIG. 1. According to an embodiment, the communication module 520 may include the first antenna 450 or the second antenna 455 of FIG. 4.

According to an embodiment, the input device 530 may receive an input from a user. For example, the input device 530 may receive from the user a command or data necessary for performing a function or a control of the electronic device. For example, the input device 530 may receive information about a reference color of an external object from the user. According to an embodiment, the input device 530 may include the input device 150 of FIG. 1. According to an embodiment, the input device 530 may include the key input devices 202, 203, and 204 of FIGS. 2 and 3.

According to an embodiment, the display device 540 may provide information visually to the user. For example, the display device 540 may provide a calibration result of the sensor module (e.g., a light sensor 551), a state of the sensor, or various pieces of information related to the sensor to the user. According to an embodiment, the display device 540 may include the display device 160 of FIG. 1. According to an embodiment, the display device 540 may include the display 220 of FIGS. 2, 3, and 4. According to an embodiment, the input device 530 and the display device 540 may be integrally formed. For example, the electronic device may include a touch screen.

According to an embodiment, the sensor module 550 may include a light sensor 551 and a motion sensor 553. According to an embodiment, the light sensor 551 may include a photoplethysmogram (PPG) sensor. According to one embodiment, the PPG sensor may be exposed through a portion of the housing of the electronic device. According to an embodiment, the PPG sensor may include a light transmission module and a receiving module that include at least one LED and at least one photodiode. According to an embodiment, the light sensor 551 may output and receive light. According to an embodiment, the light sensor 551 may convert an electrical signal to light and output the light or convert the received light to an electrical signal. For example, the light sensor 551 may output light of a specific wavelength toward the outside (e.g., the user's body) and measure light reflected from the user's body and received through the light receiving module (e.g., photodiode). According to an embodiment, the light sensor 551 may obtain biometric information of the user. For example, the light sensor 551 may analyze the output light and the received light to obtain the biometric information of the user. According to an embodiment, the light sensor 551 may output light of different wavelengths and receive light of the different wavelengths through different photodiodes under the control of the processor 560 depending on the nature of the biometric signal to be measured. For example, the light sensor 551 may output light through at least one of a plurality of LEDs and receive light through at least one of a plurality of photodiodes.

According to certain embodiments, the sensor module 550 may include various sensors capable of measuring the user's biometric signal. According to certain embodiments, the light sensor 551 may include various sensors capable of emitting or receiving light. For example, the light sensor 551 may include a laser diode (LD) or an image sensor (e.g., charge coupled device (CCD) or complementary metal oxide semiconductor image sensor (CMOS)). For example, the sensor module 550 may emit or receive light using the laser diode or the image sensor and convert the emitted or received light to electrical signals to measure the user's biometric information or convert and provide the user's biometric information to an image. According to an embodiment, the motion sensor 553 may detect movement of the electronic device. According to an embodiment, the motion sensor 553 may include an acceleration sensor, a gyro sensor, or various sensors capable of detecting movement of the electronic device. According to an embodiment, the sensor module 550 may include the sensor module 176 of FIG. 1. According to an embodiment, the sensor module 550 may include the sensor module 211 of FIGS. 2, 3, and 4.

According to an embodiment, the processor 560 may determine whether the light sensor 551 (e.g., PPG sensor) is facing a surface of an external object having a reference color. According to an embodiment, the processor 560 may output light to the external object using at least one LED included in the light sensor 551 (e.g., PPG sensor). According to an embodiment, the processor 560 may receive light reflected by the external object using a light receiving module (e.g., at least one photodiode) included in the light sensor 551 (e.g., PPG sensor). According to an embodiment, the processor 560 may recognize reflectivity of light based on the output light and received light and determine whether the light sensor 551 is facing a surface of the external object based on the determined reflectivity. For example, reflectivity of light may vary according to the color of the surface of the external object. According to an embodiment, the electronic device may include information about reflectivity of each color. For example, when the electronic device emits light of a specific wavelength or a specific color, the electronic device may store information about the amount of reflected light or reflectivity of light of the specific wavelength. The processor 560 may then compare or analyze data received from the light sensor 551 (e.g., PPG sensor) with the stored information to determine whether the surface of the external object has a particular reference color.

According to an embodiment, the processor 560 may determine whether the light sensor 551 (e.g., PPG sensor) is facing a surface of the external object based on a charging state of the battery of the electronic device. For example, when the electronic device (e.g., the battery of the electronic device) is being charged, the processor 560 may determine whether the light sensor 551 (e.g., PPG sensor) is facing a surface of an external object. For example, while the battery 470 is being charged, the processor 560 may determine whether the light sensor 551 (e.g., PPG sensor) is facing a surface of a charger having a reference color. According to an embodiment, by a user input, the processor 560 may determine the color of at least a portion of the charger at which the light sensor 551 (e.g., PPG sensor) is facing as a reference color while the electronic device is being mounted on the charger. According to an embodiment, the processor 560 may update the reference color of the external object. For example, the processor 560 may update the reference color of the external object according to a user input, a preset period, or a preset elapsed time. For example, as time elapses, the color of the external object (e.g., charger) may be changed due to the color fading, or the color may be changed due to external factors such as impact or damage. For example, when the color of the external object is changed, in order to appropriately reflect the change, the processor 560 may update the reference color. By updating the reference color, the processor 560 may accurately determine whether the light sensor 551 (e.g., PPG sensor) is facing the surface of the same external object even when the color of the external object is gradually changing.

According to an embodiment, the processor 560 may determine the execution frequency of the light sensor 551 (e.g., PPG sensor). According to an embodiment, the processor 560 may determine a test execution period of the light sensor 551 (e.g., PPG sensor) based on the execution frequency. For example, the processor 560 may determine a measurement frequency of the biometric signal of the user using the light sensor 551 (e.g., PPG sensor). The processor 560 may then determine a test execution period of the light sensor 551 (e.g., PPG sensor) based on the measurement frequency of the biometric signal. According to an embodiment, the processor 560 may determine whether the light sensor 551 (e.g., PPG sensor) is facing a surface of an external object having a reference color during the determined test execution period.

According to one embodiment, the processor 560 may determine a use frequency of each of the at least one LED or at least one photodiode included in the light sensor 551 (e.g., PPG sensor) based on the execution frequency. According to an embodiment, the processor 560 may determine a test execution period of each of the at least one LED or at least one photodiode based on the use frequency. For example, the use frequency of the LEDs or photodiodes may be different depending on the type of the biometric signal that is measured by the user. For example, the processor 560 may use the green LED in order to measure heart rate, stress, and blood pressure, the blue or infrared (IR) LED in order to measure blood sugar, and the red and IR LED in order to measure oxygen saturation. As such, the LED of the light sensor 551 (e.g., PPG sensor) that is used most frequently by the electronic device is more likely to deteriorate faster. In order to test the performance of LEDs or photodiodes of the light sensor 551 (e.g., PPG sensors) that are used at a high use frequency, the processor 560 may determine a test execution period for each LED or photodiode.

According to one embodiment, the processor 560 may determine whether to perform a test of the light sensor 551 (e.g., PPG sensor) based on a determination on whether the light sensor 551 (e.g., PPG sensor) is facing the surface of an external object having a reference color. For example, when the light sensor 551 (e.g., PPG sensor) is facing the surface of the external object, the processor 560 may perform a test of the light sensor 551 (e.g., PPG sensor). Alternatively, when the light sensor 551 (e.g., PPG sensor) is not facing the surface of the external object, the processor 560 may not perform the test of the light sensor 551 (e.g., PPG sensor) or may terminate performance of the test. For example, when the color of the external object facing the light sensor 551 (e.g., PPG sensor) differs from the reference color, the processor 560 may not perform the test of the light sensor 551 (e.g., PPG sensor) or may stop performing the test.

According to an embodiment, the processor 560 may determine whether to perform the test based on at least a portion of data from the motion sensor 553 of the electronic device. For example, the processor 560 may recognize whether the electronic device is not moving based on at least a portion of data from the motion sensor 553. For example, when there is no movement of the electronic device for a predetermined time period or more, the electronic device may start a test of the light sensor 551 (e.g., PPG sensor). Thus, the processor 560 may perform a test of the light sensor 551 (e.g., PPG sensor) while there is no movement of the electronic device, as determined based on data from the motion sensor 553. In another example, when movement of the electronic device is detected based on data from the motion sensor 553, the processor 560 may end the test of the light sensor 551 (e.g., PPG sensor).

According to one embodiment, the processor 560 operates the light sensor 551 (e.g., PPG sensor) to perform a test, during which data is received from the light sensor 551 (e.g., PPG sensor). According to an embodiment, the processor 560 may emit light through at least one LED included in the light sensor 551 (e.g., PPG sensor) and measure an amount of light received through at least one photodiode included in the light sensor 551 (e.g., PPG sensor). For example, when the light sensor 551 (e.g., PPG sensor) includes a plurality of photodiodes, the processor 560 may operate sequentially and individually the plurality of photodiodes and measure an amount of received light received by each of the plurality of photodiodes. According to an embodiment, when the electronic device emits light of a specific wavelength toward the surface of the external object having the reference color, the electronic device may store reference information about the amount of light received through a specific photodiode as a specification for that photodiode. For example, the processor 560 may emit light of a specific wavelength through the LED of the light sensor 551 (e.g., PPG sensor) and then compare the amount of light received through a photodiode included in the light sensor 551 (e.g., PPG sensor) with the stored reference information to determine a state of the photodiode. In another example, when the light sensor 551 (e.g., PPG sensor) includes a plurality of photodiodes, the processor 560 may measure the amount of light received by each of the plurality of photodiodes by sequentially operating the photodiodes and compare the amounts of light received by each of the plurality of photodiodes to determine a state of each of the plurality of photodiodes.

According to one embodiment, the processor 560 may emit light through each of the LEDs of the light sensor 551 (e.g., PPG sensor) and measure the amount of light received through a light receiving module (e.g., photodiode) included in the light sensor 551 (e.g., PPG sensor). For example, when the light sensor 551 (e.g., PPG sensor) includes a plurality of LEDs, the processor 560 may emit light sequentially and independently through each of the plurality of LEDs and measure the amount of light received by at least one photodiode included in the PPG sensor 551 (e.g., PPG sensor). According to an embodiment, when the electronic device emits light of a specific wavelength toward the surface of the external object of the reference color, the electronic device may store reference information about then amount of light received through a specific photodiode as a specification for that photodiode. For example, the processor 560 may emit light through each of the at least one LED of the light sensor 551 (e.g., PPG sensor) and then compare the amount of light received by the photodiode included in the light sensor 551 (e.g., PPG sensor) with stored reference information to determine a state of each one of the plurality of LEDs.

According to an embodiment, the processor 560 may determine an execution frequency of a function of the light sensor 551 (e.g., PPG sensor). According to one embodiment, the processor 560 may determine a use frequency of each of the LEDs or photodiodes included in the light sensor 551 (e.g., PPG sensor) based on the execution frequency of the function. According to an embodiment, the processor 560 may determine a test execution order of each of the LEDs or photodiodes based on the determined use frequency. For example, the test execution order may start with the LED and photodiode having high use frequency.

According to one embodiment, the processor 560 may perform calibration of the light sensor 551 (e.g., PPG sensor) based on at least a portion of data received from the light sensor 551 (e.g., PPG sensor). For example, the processor 560 may determine whether there is abnormality in at least one LED or at least one photodiode included in the light sensor 551 (e.g., PPG sensor) and perform calibration of the abnormal LED or photodiode. Thus, the processor 560 may increase the accuracy of the light sensor 551 (e.g., PPG sensor).

According to an embodiment, as part of the calibration, the processor 560 may change a resistance value or a gain value set for a photodiode included in the light sensor 551 (e.g., PPG sensor). For example, the processor 560 may change a resistance or gain value set for the current converted through the photodiode. In particular, when light is emitted through an emitter of the light sensor 551 e.g., LED), the amount of light received through a receiver of the light sensor 551 (e.g., light receiving module) may increase according to the intensity of the emitted light. By changing the resistance or gain value of a partial deteriorated current segment or the entire deteriorated current segment, the processor 560 may increase the measurement accuracy of the light sensor 551 (e.g., PPG sensor).

According to an embodiment, the processor 560 may provide a calibration result through a user interface. According to an embodiment, the user interface may be implemented through a display device 540, a speaker, or an LED. For example, the processor 560 may provide information of the light sensor 551 under test and a charge progress situation or information related to a time period required for the test through the display device 540. According to an embodiment, while the electronic device is being charged, the processor 560 may provide information about the test progress together with information related to charging through the user interface.

According to an embodiment, the processor 560 may provide information about a state of the light sensor 551 (e.g., PPG sensor) through the user interface. According to an embodiment, when the state of the light sensor 551 (e.g., PPG sensor) is that it cannot guarantee accuracy, the processor 560 may notify the user of this using the user interface. For example, when the light sensor 551 (e.g., PPG sensor) includes one or more LEDs or one or more photodiodes, the processor 560 may provide information about severely deteriorated LEDs or photodiodes to the user. For example, the processor 560 may provide notification through the user interface (e.g., the display device 540) that the performance of a specific device (LED or photodiode) has declined because it is severely damaged. The processor 560 may provide a notification recommending a visit to a service center or an after-sales service. According to one embodiment, the processor 560 may provide information of a service center related to user information (e.g., address of a service center close to a current location or the user's home address).

According to an embodiment, the processor 560 may include the processor 120 of FIG. 1.

An electronic device (e.g., the electronic device 101 of FIG. 1, the electronic device 200 of FIGS. 2 and 3, the electronic device 400 of FIG. 4, and the electronic device 500 of FIG. 5) according to an embodiment of the disclosure may include a housing (e.g., the housing 210 of FIGS. 2 and 3); a rechargeable battery (e.g., the battery 189 of FIG. 1, the battery 470 of FIG. 4, the charging module 510 of FIG. 5); a user interface (e.g., the display device 160, the audio output device 155, or the interface 177 of FIG. 1, the audio modules 205 and 208 of FIGS. 2 and 3, the display 220 of FIG. 4, and the display device 540 of FIG. 5); a photoplethysmogram (PPG) sensor (e.g., the sensor module 176 of FIG. 1, the sensor module 211 of FIG. 3, and the light sensor 551 of FIG. 5) including a light receiving module exposed through a portion of the housing, at least one LED, and at least one photodiode; a processor (e.g., the processor 120 of FIG. 1, the processor 560 of FIG. 5) operatively connected to the battery, the user interface, and the PPG sensor; and a memory (e.g., the memory 130 of FIG. 1) operatively connected to the processor. According to one embodiment, the memory may store instructions that, when executed, cause the processor to determine whether the PPG sensor is facing a surface of an external object having a reference color, to determine to perform a test of the PPG sensor based on whether the PPG sensor is facing the surface, to receive data from the PPG sensor by operating the PPG sensor in response to determining to perform the test, and to perform a calibration of the PPG sensor based on at least a portion of the received data.

According to an embodiment, the instructions may further cause the processor to determine whether the PPG sensor is facing the surface based on whether the battery is being charged.

According to an embodiment, the electronic device may further include a motion sensor (e.g., the sensor module 176 of FIG. 1, the sensor module 211 of FIG. 3, and the motion sensor 553 of FIG. 5). According to an embodiment, the instructions may further cause the processor to determine whether to perform the test based on at least a portion of data from a motion sensor of the electronic device.

According to an embodiment, the instructions may further cause the processor to provide a result of the calibration through the user interface.

According to an embodiment, the user interface may be implemented through at least one of a display (e.g., the display device 160 of FIG. 1, the display 220 of FIG. 4, and the display device 540 of FIG. 5), a speaker (e.g., the sound output device 155 of FIG. 1 and the audio modules 205 and 208 of FIGS. 2 and 3), or a light emitting diode (LED).

According to an embodiment, the instructions may further cause the processor to provide information about a state of the PPG sensor through the user interface.

According to one embodiment, the instructions may further cause the processor to output light to the external object through the at least one LED, to receive light reflected by the external object through the light receiving module, to determine reflectivity of light based on the output light and the received light, and to determine whether the PPG sensor is facing a surface of an external object having the reference color based on the reflectivity of the light.

According to an embodiment, the instructions may further cause the processor to determine an execution frequency of a function of the PPG sensor and to determine a test execution period of the PPG sensor based on the execution frequency.

According to one embodiment, the instructions may further cause the processor to determine a use frequency of at least one LED or at least one photodiode included in the PPG sensor based on the execution frequency and to determine a test execution period or test execution order of the at least one LED or the at least one photodiode based on the use frequency.

According to an embodiment, the instructions may further cause the processor to change a resistance value or a gain value set for the at least one photodiode as at least a portion of the calibration.

Figure 6A:
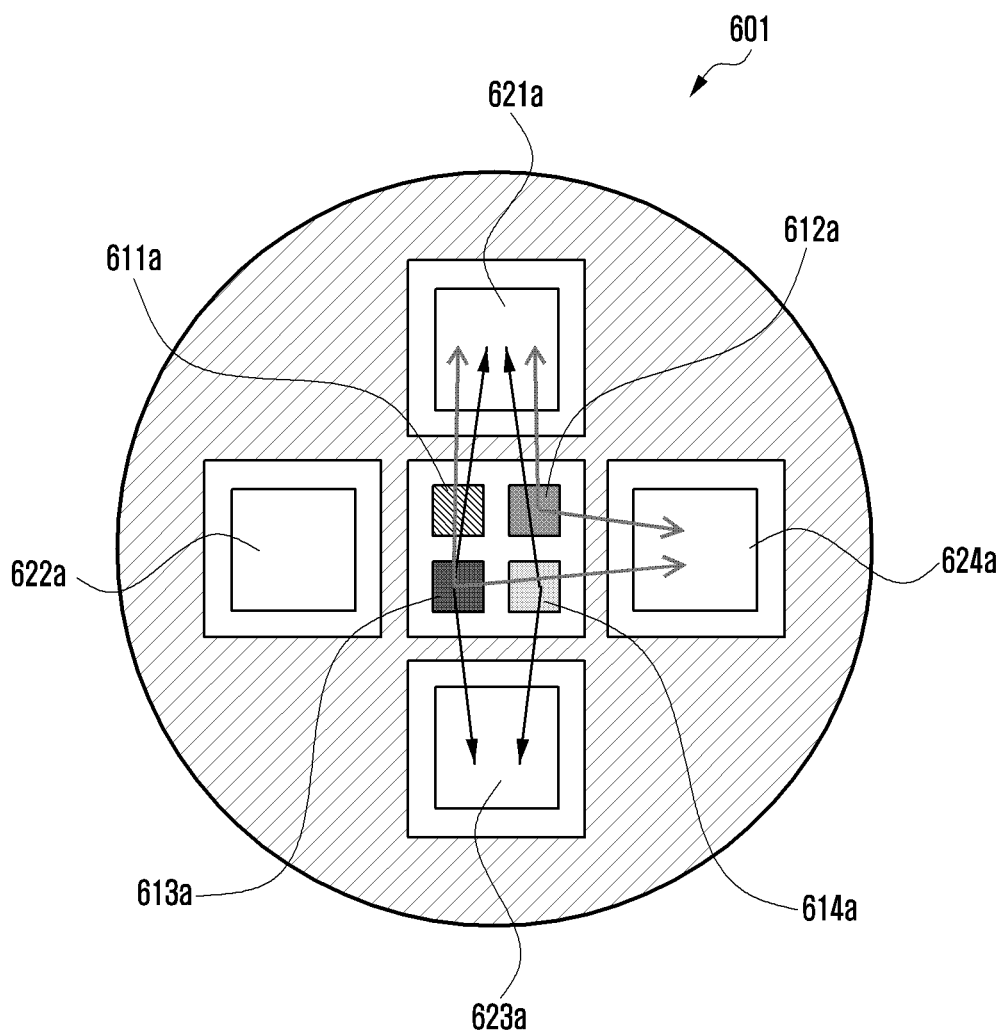
FIG. 6A and FIG. 6B are views illustrating structures of a photoplethysmogram (PPG) sensor of an electronic device according to certain embodiments of the disclosure.
Figure 6B:
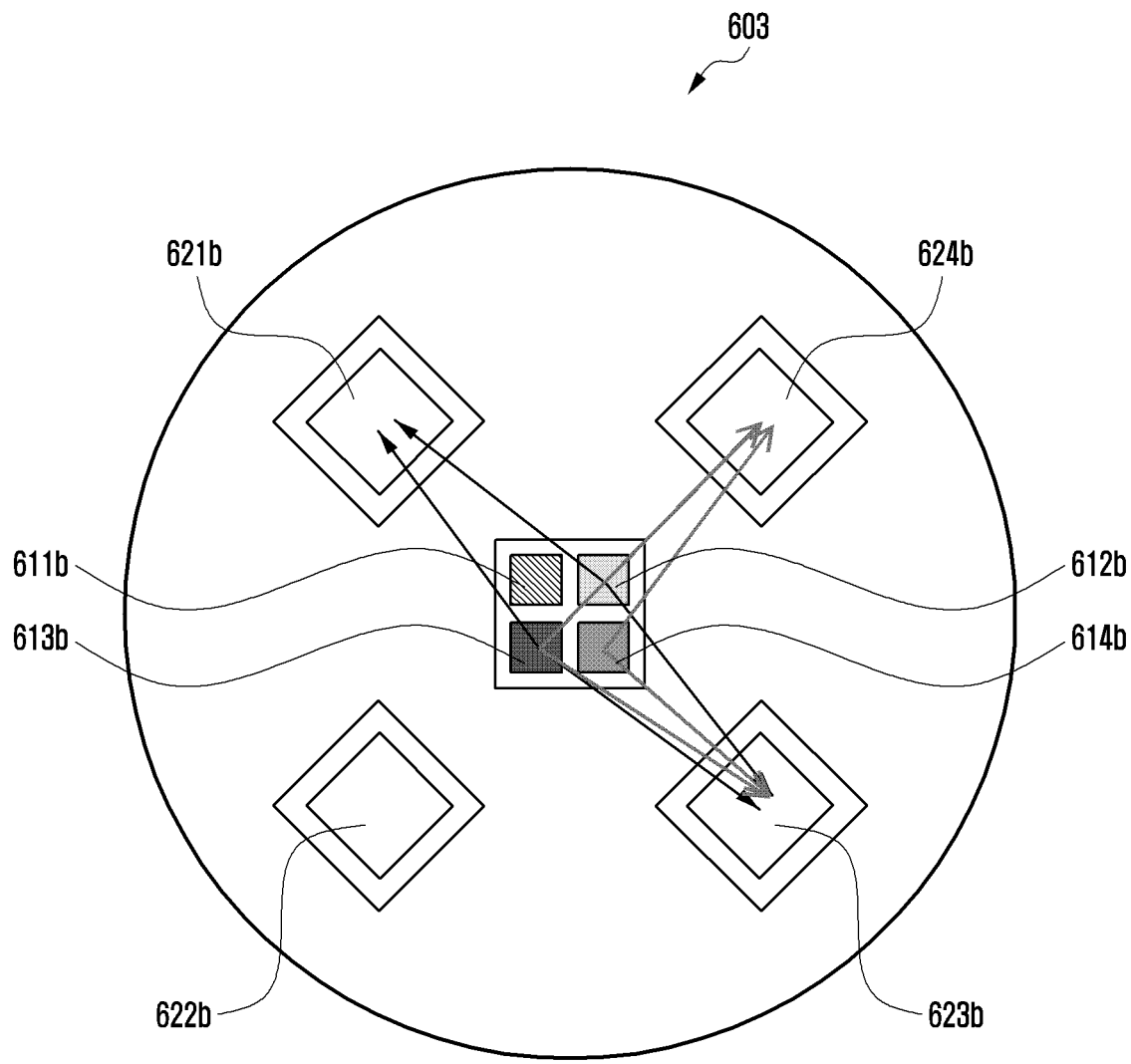

FIGS. 6A and 6B are views illustrating structures of a photoplethysmogram (PPG) sensor of an electronic device according to certain embodiments of the disclosure.

According to one embodiment, an electronic device (e.g., the electronic device 101 of FIG. 1, the electronic device 200 of FIGS. 2 and 3, the electronic device 400 of FIG. 4, and the electronic device 500 of FIG. 5) may include PPG sensors 601 and 603. According to one embodiment, the PPG sensors 601 and 603 (e.g., the sensor module 176 of FIG. 1, the sensor module 211 of FIG. 3, and the light sensor 551 of FIG. 5) may be exposed through a part of the housing of the electronic device. According to one embodiment, the PPG sensors 601 and 603 may include at least one of the LEDs 611a, 611b, 612a, 612b, 613a, 613b, 614a, and 614b and at least one of the photodiodes 621a, 621b, 622a, 622b, 623a, 623b, 624a, and 624b. According to an embodiment, the electronic device may obtain the user's biometric information through the PPG sensors 601 and 603. For example, the electronic device may emit light using LEDs 611a, 611b, 612a, 612b, 613a, 613b, 614a, and 614b of the PPG sensors 601 and 603 and receive light reflected by the user's body using photodiodes 621a, 621b, 622a, 622b, 623a, 623b, 624a, and 624b. According to an embodiment, the electronic device may analyze light emitted and received by the PPG sensors 601 and 603 to obtain the user's biometric information. According to an embodiment, the electronic device may provide a health related function based on the user's biometric information obtained using the PPG sensors 601 and 603. For example, the electronic device may measure the user's heart rate, oxygen saturation, stress, blood pressure, sleep stage (sleep state), and/or blood sugar based on data obtained from the PPG sensors 601 and 603.

According to an embodiment, in order to increase measurement accuracy, the PPG sensors 601 and 603 of the electronic device may include a plurality of LEDs 611a, 611b, 612a, 612b, 613a, 613b, 614a, and 614b or a plurality of photodiodes 621a, 621b, 622a, 622b, 623a, 623b, 624a, and 624b. For example, when a green LED (wavelength of about 520 to 560 nm) or a blue LED (wavelength of about 460 nm) is used, the emitted light does not respond sensitively to the user's movement, but transmittance through the user's skin may be low. Alternatively, when a red LED (wavelength of about 660 nm) or an infrared LED (wavelength of about 880 to 940 nm) is used, the emitted light may have high transmittance through the user's skin, but respond sensitively to the user's movement. Thus, the electronic device may increase accuracy of measurement by using multi-LEDs 611a, 611b, 612a, 612b, 613a, 613b, 614a, and 614b or multi photodiodes 621a, 621b, 622a, 622b, 623a, 623b, 624a, and 624b.

FIG. 6A illustrates a case in which the PPG sensor 601 includes four LEDs 611a, 612a, 613a, and 614a and four photodiodes 621a, 622a, 623a, and 624a. The four LEDs output light of different wavelengths. For example, the PPG sensor 601 of the electronic device may include a first LED 611a for emitting green light, a second LED 612a for emitting blue light, a third LED 613a for emitting infrared light, and a fourth LED 614a for emitting red light. In this example, the first LED 611a, the second LED 612a, the third LED 613a, and the fourth LED 614a may be disposed in a lattice pattern at a center portion of the PPG sensor 601. Further, the PPG sensor 601 of the electronic device may include a first photodiode 621a, second photodiode 622a, third photodiode 623a, and fourth photodiode 624a. According to an embodiment, the first to fourth photodiodes 621a, 622a, 623a, and 624a may be distributed and disposed inside the PPG sensor 601 so as to receive light from various directions. For example, the first photodiode 621a may be disposed at the upper end of the first to fourth LEDs 611a, 612a, 613a, and 614a; the second photodiode 622a may be disposed at the left side of the first to fourth LEDs 611a, 612a, 613a, and 614a; the third photodiode 623a may be disposed at the lower end of the first to fourth LEDs 611a, 612a, 613a, and 614a; and the fourth photodiode 624a may be disposed at the right side of the first to fourth LEDs 611a, 612a, 613a, and 614a.

According to one embodiment, the PPG sensor 601 may emit light from at least one LED 611a, 612a, 613a, and 614a and receive light through at least one photodiode 621a, 622a, 623a, and 624a. According to an embodiment, the electronic device may selectively use different LEDs or different photodiodes depending on the desired function of the sensor. For example, when the user wants to measure the user's blood sugar, the electronic device may emit light using the second LED 612a and the third LED 613a and receive reflected light using the first photodiode 621a and the fourth photodiode 624a. In another example, when the user wants to measure oxygen saturation, the electronic device may emit light using the third LED 613a and the fourth LED 614a and receive reflected light using the first photodiode 621a and the third photodiode 623a. In yet another example, when measuring a heart rate, stress, or blood pressure of the user, the electronic device may use the first LED 611a for emitting green light. In still yet another example, when measuring blood sugar of the user, the electronic device may use the second LED 612a for emitting blue light and/or the third LED 613a for emitting infrared light. In still yet another example, when measuring the user's oxygen saturation, the electronic device may use the fourth LED 614a for emitting blue light and/or the third LED 613a for emitting infrared light. In still yet another example, when the electronic device measures the user's sleep state, the electronic device may use at least one of the first LED 611a for outputting green light, the third LED 613a for outputting infrared light, or the fourth LED 614a for outputting red light.

According to various embodiments, at least one LED 611a, 611b, 612a, 612b, 613a, 613b, 614a, and 614b and at least one photodiode 621a, 621b, 622a, 622b, 623a, 623b, 624a, and 624b included in the PPG sensors 601 and 603 may be disposed in various forms or structures. FIG. 6B illustrates a structure in which the PPG sensor 603 includes four LEDs 611b, 612b, 613b, and 614b for outputting light of different wavelengths and four photodiodes 621b, 622b, 623b, and 624b. FIG. 6B illustrates a sensor in which the four LEDs 611b, 612b, 613b, and 614b and the four photodiodes 621b, 622b, 623b, and 624b are disposed differently from in FIG. 6A.

For example, the PPG sensor 603 may include a fifth LED 611b for emitting green light, a sixth LED 612b for emitting red light, a seventh LED 613b for emitting infrared light, and an eighth LED 614b for emitting blue light. In this example, the fifth LED 611b, the sixth LED 612b, the seventh LED 613b, and the eighth LED 614b may be disposed in a central portion of the PPG sensor 603 in a lattice pattern. The PPG sensor 603 of the electronic device may include a fifth photodiode 621b, a sixth photodiode 622b, a seventh photodiode 623b, and an eighth photodiode 624b. According to an embodiment, the fifth to eighth photodiodes 621b, 622b, 623b, and 624b may be distributed and disposed inside the PPG sensor 603 so as to receive light from various directions. For example, the fifth photodiode 621b may be disposed at the upper left of the fifth to eighth LEDs 611b, 612b, 613b, and 614b; the sixth photodiode 622b may be disposed at the lower left of the fifth to eighth LEDs 611b, 612b, 613b, and 614b; the seventh photodiode 623b may be disposed at the lower right of the fifth to eighth LEDs 611b, 612b, 613b, and 614b; and the eighth photodiode 624b may be disposed at the upper right of the fifth to eighth LEDs 611b, 612b, 613b, and 614b.

According to an embodiment, when the user wants to measure the user's blood sugar, the electronic device may emit light using the seventh LED 613b and the eighth LED 614b and receive reflected light using the seventh photodiode 623b and the eighth photodiode 624b. According to an embodiment, when the user wants to measure oxygen saturation of the user, the electronic device may emit light using the sixth LED 612b and the seventh LED 613b and receive reflected light using the fifth photodiode 621b and the seventh photodiode 623b.

According to various other embodiments, the number and disposition of LEDs and photodiodes included in the PPG sensor of the electronic device are not limited to those illustrated in FIGS. 6A and 6B and may be variously changed.

Figure 7:
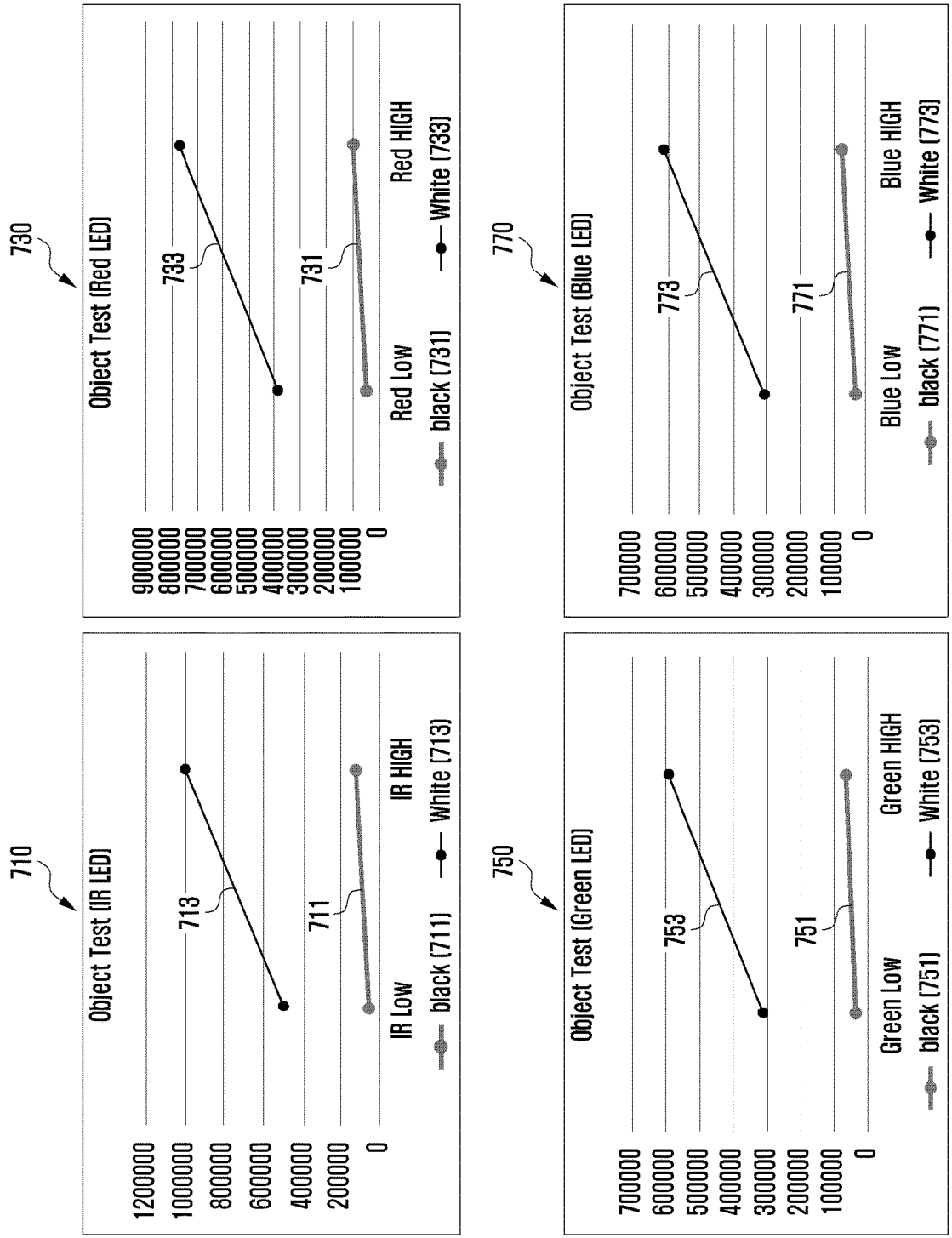
FIG. 7 is a graph illustrating an operation of an electronic device according to an embodiment of the disclosure.

FIG. 7 is a graph illustrating an operation of an electronic device according to an embodiment of the disclosure.

According to one embodiment, an electronic device (e.g., the electronic device 101 of FIG. 1, the electronic device 200 of FIGS. 2 and 3, the electronic device 400 of FIG. 4, and the electronic device 500 of FIG. 5) may determine whether a PPG sensor (e.g., the sensor module 176 of FIG. 1, the sensor module 211 of FIG. 3, the light sensor 551 of FIG. 5, and the PPG sensors 601 and 603 of FIGS. 6A and 6B) is facing a surface of an external object having a reference color. For example, the external object may be a charger of the electronic device or an external object (e.g., table) in which the electronic device is placed. For example, the reference color may be preset or may be set according to the user's input.

According to an embodiment, the electronic device may determine whether to perform a test of the PPG sensor depending on whether the PPG sensor is facing a surface of an external object having a reference color. For example, when the PPG sensor is facing the surface, the electronic device may perform the test of the PPG sensor.

According to an embodiment, the electronic device may output light to the external object using at least one LED included in the PPG sensor and receive light reflected by the external object using a light receiving module (e.g., at least one photodiode) included in the PPG sensor. According to an embodiment, the electronic device may recognize reflectivity of light based on the output light and the received light. According to an embodiment, the electronic device may determine whether the PPG sensor is facing the surface of the external object having the reference color based on the reflectivity of light.

For example, reflectivity of light may vary according to the color of the surface of the external object. That is, when the electronic device emits light of a specific wavelength toward the external object, the amount of light received by the electronic device may vary according to the color of the surface of the external object. According to an embodiment, the electronic device may store information about reflectivity of a variety of colors. For example, when the electronic device emits light of a specific wavelength or a specific color to the external device, the electronic device may store information about the amount of light reflected and received from the external device, where the amount of light is dependent on the color of the external device.

For example, 710 is a graph illustrating an amount 711 of received light when infrared light is emitted to a surface of a black external object and an amount 713 of received light when infrared light is emitted to a surface of a white external object. 730 is a graph illustrating an amount 731 of received light when red light is emitted to the surface of the black external object and an amount 733 of received light when red light is emitted to the surface of the white external object. 750 is a graph illustrating an amount 751 of received light when green light is emitted to the surface of the black external object and an amount 753 of received light when green light is emitted to the surface of the white external object. 770 is a graph illustrating an amount 771 of received light when blue light is emitted to the surface of the black external object and an amount 773 of received light when blue light is emitted to the surface of the white external object. The Y-axis of the graphs 710, 730, 750 and 770 may indicate a digital value regarding the amount of light received by the photodiode. For example, the processor may convert light received through the photodiode into a current. The processor may calculate the voltage value using the converted current and the set resistance value (or gain value). The processor may convert the calculated voltage value into a digital value through an ADC (analog to digital converter). The Y-axis of the graphs 710, 730, 750 and 770 may indicate a value obtained by converting the amount of light received by the photodiode into a digital value.

For example, with reference to 710, 730, 750, and 770, when light of different wavelengths (different colors) are emitted at different intensities, a varying amount of light reflected and received by an external object may be determined. For example, with reference to 710, 730, 750, and 770, when the color of the external object is constant, the output graphs across different wavelengths (e.g. 711, 731, 751, and 771) are approximate the same with slight differences. According to one embodiment, the electronic device may emit light through at least one LED of the PPG sensor and determine the color of a surface of the external object facing the PPG sensor. The electronic device may do so by measuring the amount of light reflected by the external object and received through at least one photodiode. For example, the electronic device may determine whether the PPG sensor is facing the surface of the external object having a reference color by determining the color of at least a portion of the external object that the PPG sensor is facing.

According to an embodiment, the electronic device may determine whether to perform a test based on at least a portion of data from the motion sensor. For example, the electronic device may recognize whether the electronic device is moving based on at least a portion of data from the motion sensor. For example, when the electronic device is moving, it may indicate that the user is using the electronic device and it may be difficult to accurately test the PPG sensor. On the other hand, when there is no movement of the electronic device for a predetermined time period or more based on data from the motion sensor, the electronic device may start a test of the PPG sensor. As such, the electronic device may perform a test of the PPG sensor while there is no movement of the electronic device based on the data from the motion sensor. Alternatively, when movement of the electronic device is detected based on the data from the motion sensor, the electronic device may end the test of the PPG sensor.

According to an embodiment, the electronic device may determine whether the PPG sensor is facing a surface of the external object based on whether the battery of the electronic device is being charged. For example, when the electronic device is being charged, the electronic device may determine whether the PPG sensor is facing a surface of the external object. When the electronic device is connected to an external charger (e.g. via a charging wire) or mounted on an external charger (e.g., charging dock), these conditions may indicate that the electronic device is not currently in use and/or the device is not moving. In this case, the electronic device may determine whether the PPG sensor is facing a surface of the charger having a reference color while the device is being charged. For example, when the charger is black, the electronic device may determine that the PPG sensor is facing a black surface of the charger. In another example, when the charger is white, the electronic device may determine that the PPG sensor is facing a white surface of the charger. According to an embodiment, the electronic device may set, by a user input, the color of at least a portion of the charger that the PPG sensor is facing to a reference color while the electronic device is mounted on the charger.

Figure 8:
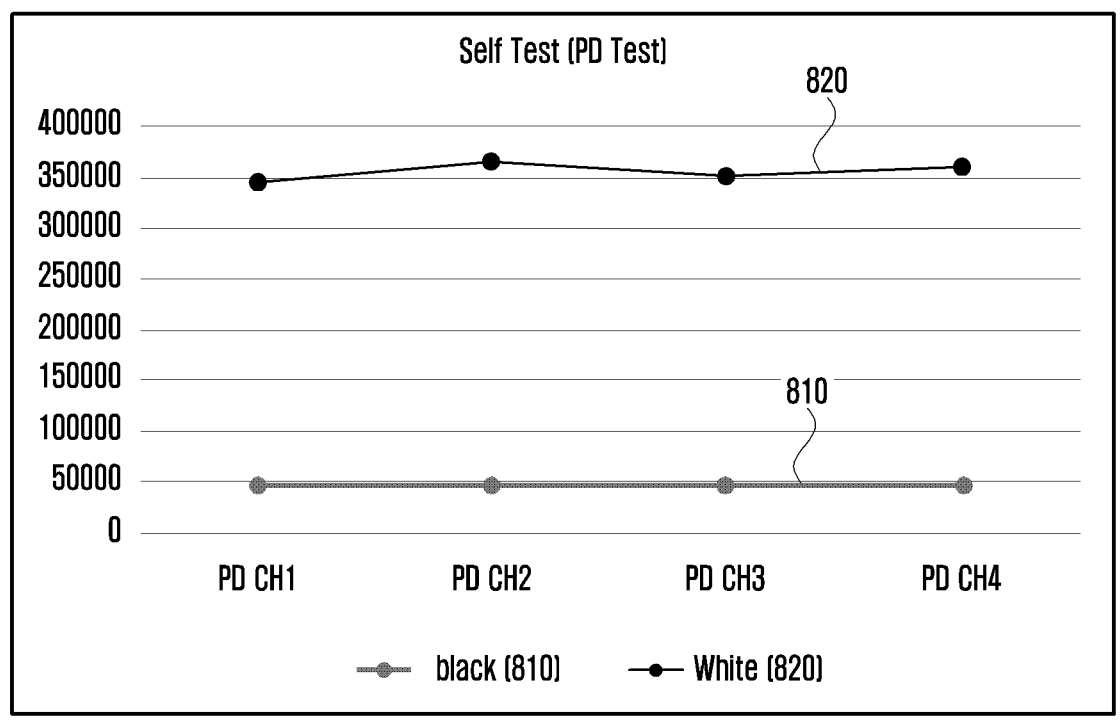
FIG. 8 is a graph illustrating a photodiode test operation of an electronic device according to an embodiment of the disclosure.

FIG. 8 is a graph illustrating a photodiode test operation of an electronic device according to an embodiment of the disclosure. For example, FIG. 8 is a graph illustrating a result in which an electronic device (e.g., the electronic device 101 of FIG. 1, the electronic device 200 of FIGS. 2 and 3, the electronic device 400 of FIG. 4, and the electronic device 500 of FIG. 5) tests photodiodes of a PPG sensor (e.g., the sensor module 176 of FIG. 1, the sensor module 211 of FIG. 3, the light sensor 551 of FIG. 5, and the PPG sensors 601 and 603 of FIGS. 6A and 6B). The Y-axis of the graph shown in FIG. 8 may indicate a digital value regarding the amount of light received by the photodiode. For example, the processor may convert light received through the photodiode into a current. The processor may calculate the voltage value using the converted current and the set resistance value (or gain value). The processor may convert the calculated voltage value into a digital value through an ADC (analog to digital converter). The Y-axis of the graph shown in FIG. 8 may indicate a value obtained by converting the amount of light received by the photodiode into a digital value.

According to an embodiment, the electronic device may emit light through at least one LED of the PPG sensor and measure the amount of light received through at least one photodiode PD CH1, PD CH2, PD CH3, and PD CH4 included in the PPG sensor. For example, when the PPG sensor includes a plurality of photodiodes PD CH1, PD CH2, PD CH3, and PD CH4, the electronic device may operate the plurality of photodiodes PD CH1, PD CH2, PD CH3, and PD CH4 sequentially and individually to measure the amount of received light in each photodiode. For example, when light is emitted through an infrared LED, FIG. 8 illustrates an amount 810 of light reflected by a black external object and received through each of the photodiodes PD CH1, PD CH2, PD CH3, and PD CH4 and an amount 820 of light reflected by a white external object and received through each of the photodiodes PD CH1, PD CH2, PD CH3, and PD CH4. According to an embodiment, when the electronic device emits light of a specific wavelength toward a surface of an external object having a reference color, the electronic device may store reference information about the amount of light received through a particular photodiode as, for example, a specification for that photodiode. For example, the electronic device may emit light of a specific wavelength using the LED of the PPG sensor and then compare the amount of light received by the at least one photodiode included in the PPG sensor with stored reference information to determine a state of at least one photodiode. According to an embodiment, when the PPG sensor includes a plurality of photodiodes PD CH1, PD CH2, PD CH3, and PD CH4, the electronic device may measure the amount of received light individually received by the plurality of photodiodes PD CH1, PD CH2, PD CH3, and PD CH4 and compare the amounts of light received through each of the plurality of photodiodes PD CH1, PD CH2, PD CH3, and PD CH4 to each other determine the states of each of the plurality of photodiodes PD CH1, PD CH2, PD CH3, and PD CH4. For example, in FIG. 8, holding the colors of the external object constant (e.g., the black external object or the white external object), if light of the same wavelength is emitted, it may be determined that there is no large deviation in the amount of light received through each of the first photodiode PD CH1, the second photodiode PD CH2, the third photodiode PD CH3, and the fourth photodiode PD CH4. When there is no large deviation in the amount of light received by each of the photodiodes PD CH1, PD CH2, PD CH3, and PD CH4, the electronic device may recognize that each of the photodiodes PD CH1, PD CH2, PD CH3, and PD CH4 is in a normal state. But when a particular photodiode receives an amount of light different from that of the remaining photodiodes, the electronic device may recognize that there is a problem in that photodiode. As show in FIG. 8, the amount of variation in the graph 820 may indicate that one of more of the photodiodes is in an abnormal state. As such, the electronic device may compare the stored reference information with the amount of light received by the photodiodes to recognize a state of individual photodiodes.

Figure 9:
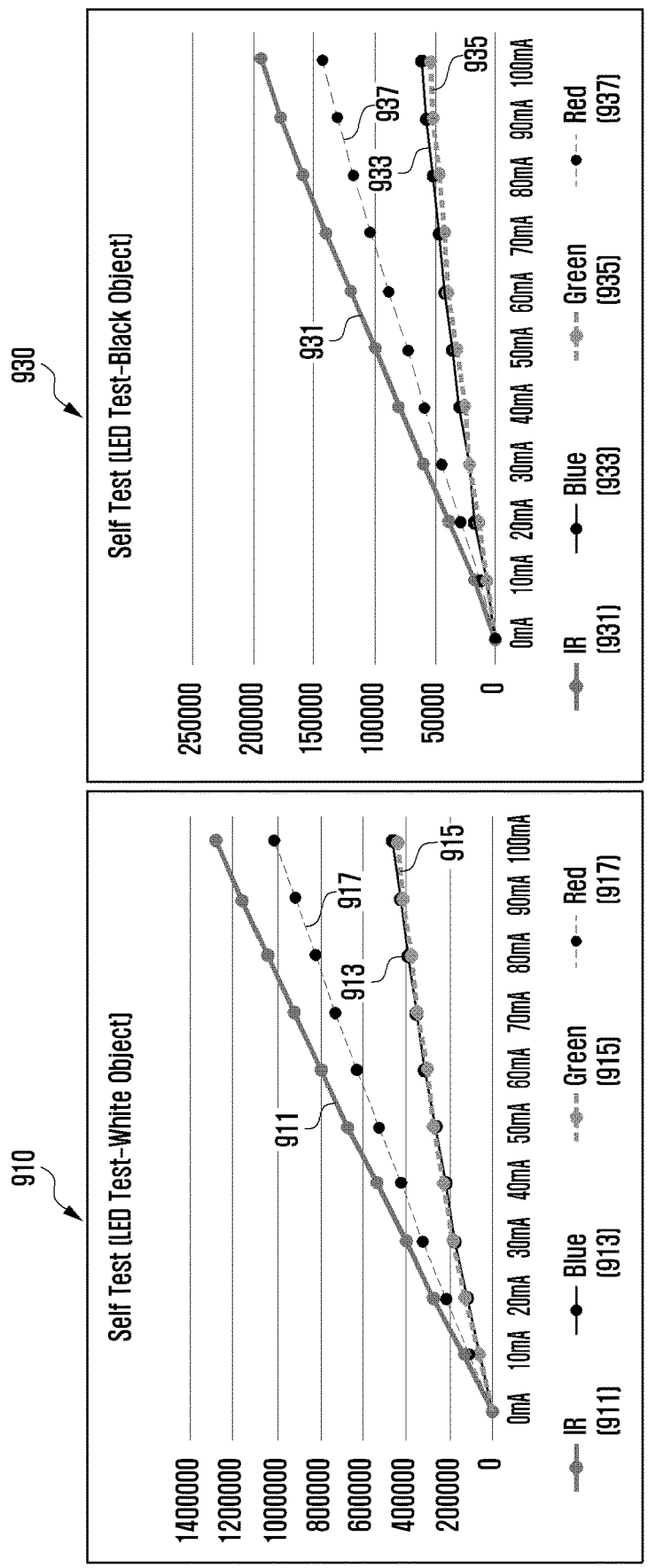
FIG. 9 is a graph illustrating an LED test operation of an electronic device according to an embodiment of the disclosure.

FIG. 9 is a graph illustrating an LED test operation of an electronic device according to an embodiment of the disclosure. For example, FIG. 9 is a graph illustrating the amount of light in which an electronic device (e.g., the electronic device 101 of FIG. 1, the electronic device 200 of FIGS. 2 and 3, the electronic device 400 of FIG. 4, and the electronic device 500 of FIG. 5) emits using each of the LEDs included in the PPG sensor (e.g., the sensor module 176 of FIG. 1, the sensor module 211 of FIG. 3, the light sensor 551 of FIG. 5, and the PPG sensors 601 and 603 of FIGS. 6A and 6B), and also the amount of light reflected by an external object and received by a photodiode. For example, when light is emitted using an LED (IR LED 911) for emitting infrared light, an LED (Blue LED 913) for emitting blue light, an LED (Green LED 915) for emitting green light, and an LED (Red LED 917) for emitting red light, 910 illustrates the amount of light reflected by a white external object and received by a specific photodiode. In another example, when light is emitted through an LED (IR LED 931) for emitting infrared light, an LED (Blue LED 933) for emitting blue light, an LED (Green LED 935) for emitting green light, and an LED (Red LED 937) for emitting red light, 930 illustrates an amount of light reflected by a black external object and received by a specific photodiode. The Y-axis of the graphs 910 and 930 may indicate a digital value regarding the amount of light received by the photodiode. The Y-axis of the graphs 910 and 930 may indicate a value obtained by converting the amount of light received by the photodiode into a digital value.

According to one embodiment, the electronic device may emit light through each (IR LEDs 911 and 931, blue LEDs 913 and 933, green LEDs 915 and 935, and red LEDs 917 and 937) LED of the PPG sensor and measure the amount of light received by a light receiving module (e.g., photodiode) included in the PPG sensor. For example, when the PPG sensor includes a plurality of LEDs (IR LEDs 911 and 931, blue LEDs 913 and 933, green LEDs 915 and 935, and red LEDs 917 and 937), the electronic device may operate each LED (IR LEDs 911 and 931, blue LEDs 913 and 933, green LEDs 915 and 935, and red LEDs 917 and 937) sequentially and independently through to emit light. The electronic device may then measure the amount of received light using at least one photodiode included in the PPG sensor. For example, the amount of light reflected by an external object of a specific color, when analyzed with respect to intensity of light emitted in a specific wavelength (i.e., color of light), may have a particular slope. The amount of received light relative to the intensity of the emitting light may have different slopes depending on the color of the external object. According to an embodiment, when the electronic device emits light of a specific wavelength toward a surface of the external object having a reference color, the electronic device may store reference information about the amount of light received through a specific photodiode as, for example, a specification of that LED. For example, after emitting light through each LED (IR LEDs 911 and 931, Blue LEDs 913 and 933, Green LEDs 915 and 935, and Red LEDs 917 and 937) of the PPG sensor, the electronic device may compare the amount of light received through at least one photodiode included in the PPG sensor with the stored reference information to determine a state of each LED (IR LEDs 911 and 931, Blue LEDs 913 and 933, green LEDs 915 and 935, and red LEDs 917 and 937).

Figure 10A:
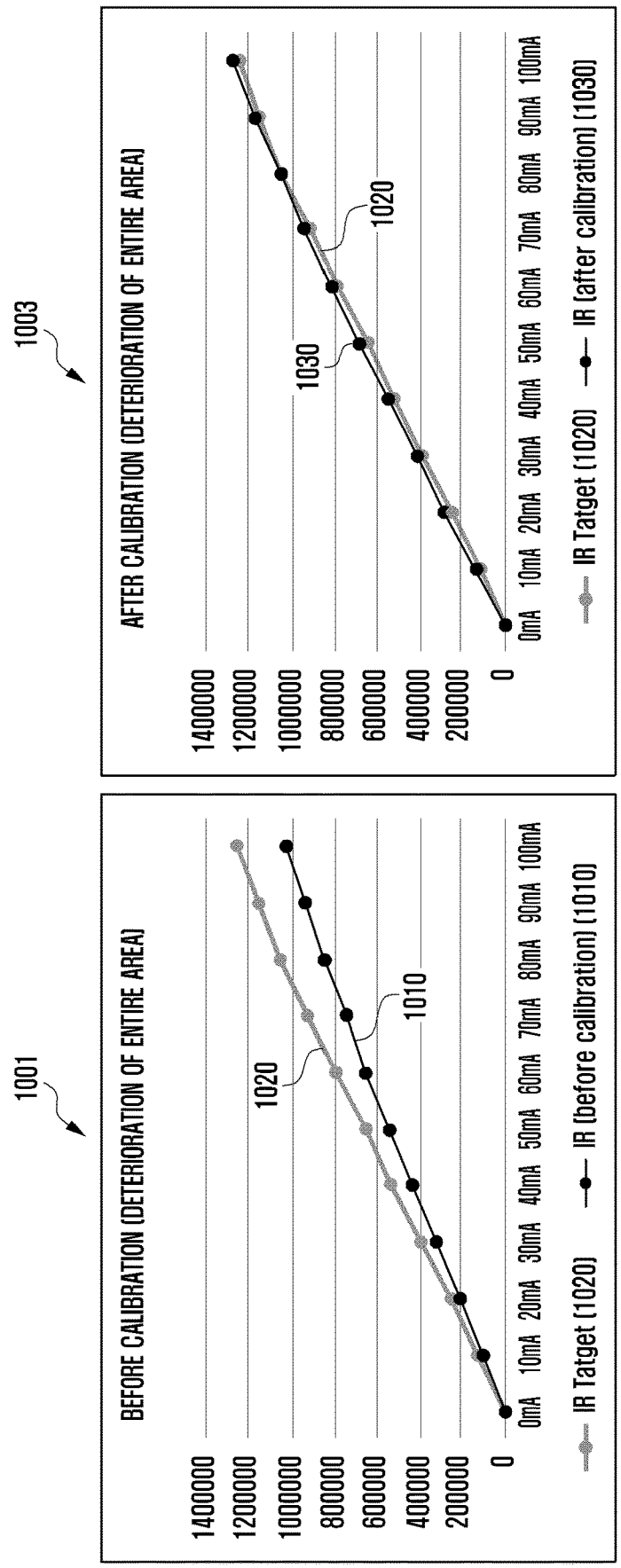
FIGS. 10A and 10B are graphs illustrating a calibration operation of an electronic device according to certain embodiments of the disclosure.
Figure 10B:
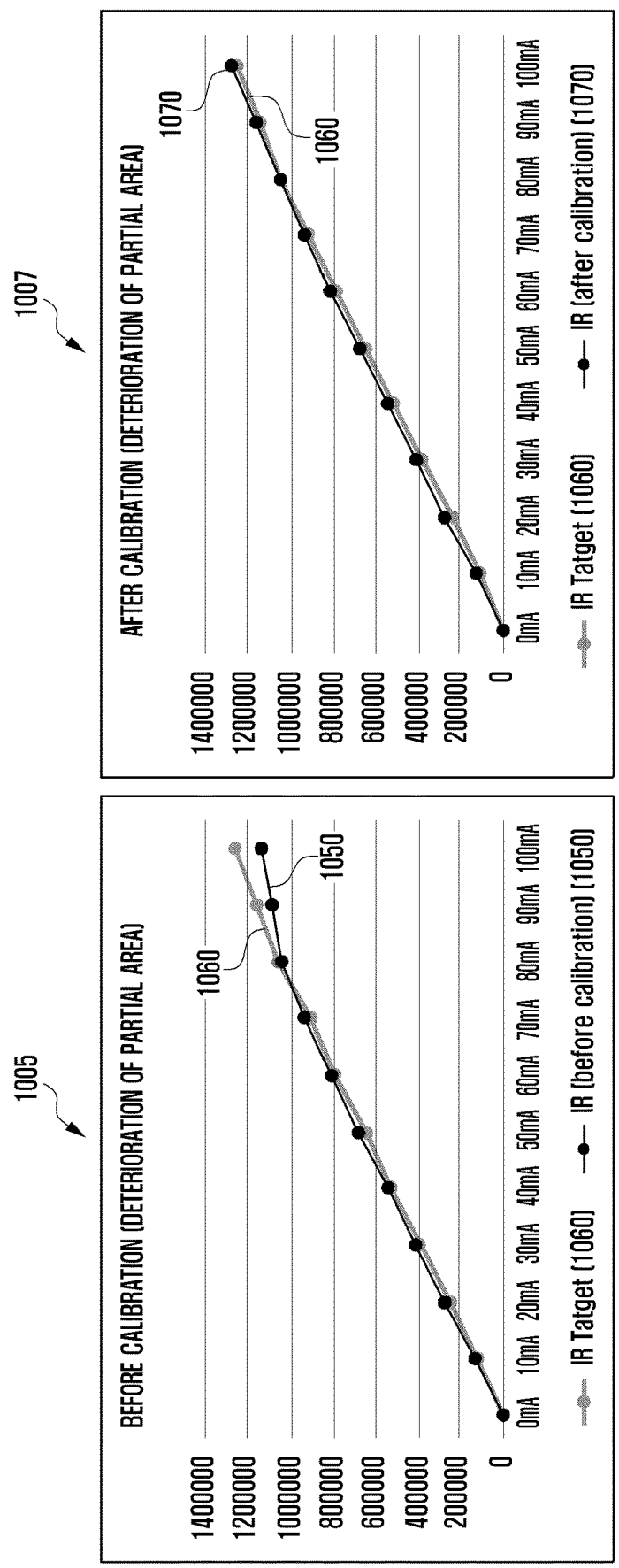

FIGS. 10A and 10B are graphs illustrating a calibration operation of an electronic device according to certain embodiments of the disclosure. The Y-axis of the graphs shown in FIGS. 10A and 10B may indicate a digital value regarding the amount of light received by the photodiode. For example, the processor may convert light received through the photodiode into a current. The processor may calculate the voltage value using the converted current and the set resistance value (or gain value). The processor may convert the calculated voltage value into a digital value through an ADC (analog to digital converter). The Y-axis of the graphs shown in FIGS. 10A and 10B may indicate a value obtained by converting the amount of light received by the photodiode into a digital value.

According to one embodiment, an electronic device (e.g., the electronic device 101 of FIG. 1, the electronic device 200 of FIGS. 2 and 3, the electronic device 400 of FIG. 4, and the electronic device 500 of FIG. 5) may receive data from a PPG sensor (e.g., the sensor module 176 of FIG. 1, the sensor module 211 of FIG. 3, the light sensor 551 of FIG. 5, and the PPG sensors 601 and 603 of FIGS. 6A and 6B) and perform calibration of the PPG sensor based on at least a portion of the received data. According to an embodiment, the electronic device may change a resistance value or a gain value set to at least one photodiode included in the PPG sensor as at least a portion of the calibration. As described above, the electronic device may convert light received through the photodiode to an electrical signal (e.g., current). In an example of calibration, the electronic device may change the resistance value or the gain value set for the current converted through the photodiode. For example, by changing the preset resistance value or gain value, the electronic device may change the current value of the photodiode.

For example, FIG. 10A is a graph illustrating a current value of a photodiode before and after a calibration operation when the entire current segment of the photodiode has deteriorated. When light is emitted through a PPG sensor (e.g., LED) of the electronic device, the amount of light received through the PPG sensor (e.g., light receiving module or photodiode) may increase according to the intensity of the emitted light. For example, the amount of light received through the photodiode (or the current value converted from light received in the photodiode) may increase in proportion to the current value applied to the LED. With reference to 1001, when deterioration occurs in the entire current segment of the particular LED (e.g., the infrared LED in FIG. 10A), the amount 1010 of received light before calibration may be reduced, compared with a characteristic graph (IR target) 1020 of normal LEDs. According to an embodiment, by changing the resistance value or the gain value set for the photodiode, the electronic device may correct the error caused by deterioration of the LED or the photodiode. For example, with reference to 1003, the electronic device may change the resistance value or the gain value set for the current converted through the photodiode for the entire current segment shown in the figure, thereby compensating for the deterioration of the LED or photodiode, as in the graph (IR) 1030 after calibration.

In another example, when the PPG sensor has deteriorated only in a specific current segment, FIG. 10B illustrates characteristics of the PPG sensor before and after calibration. With reference to 1005, when deterioration occurs in a partial current segment (e.g., a specific segment of about 80 mA or more) of a specific LED (e.g., the infrared LED of FIG. 10B) included in the PPG sensor, the amount 1050 of received IR light before calibration may be reduced only in the partial segment, compared with a characteristic graph (IR target) 1060 of the normal LED. According to an embodiment, when the electronic device recognizes that performance has deteriorated only in the partial segment, the electronic device may selectively change a resistance value or a gain value set for the PPG sensor (e.g., light receiving module or photodiode) in only the corresponding segment. For example, with reference to 1007, the electronic device changes the resistance value or the gain value set for the photodiode for a specific current segment (i.e., partial deterioration area), thereby compensating for the deterioration of the LED or photodiode, as in the graph (IR) 1070 after calibration.

Figure 11:
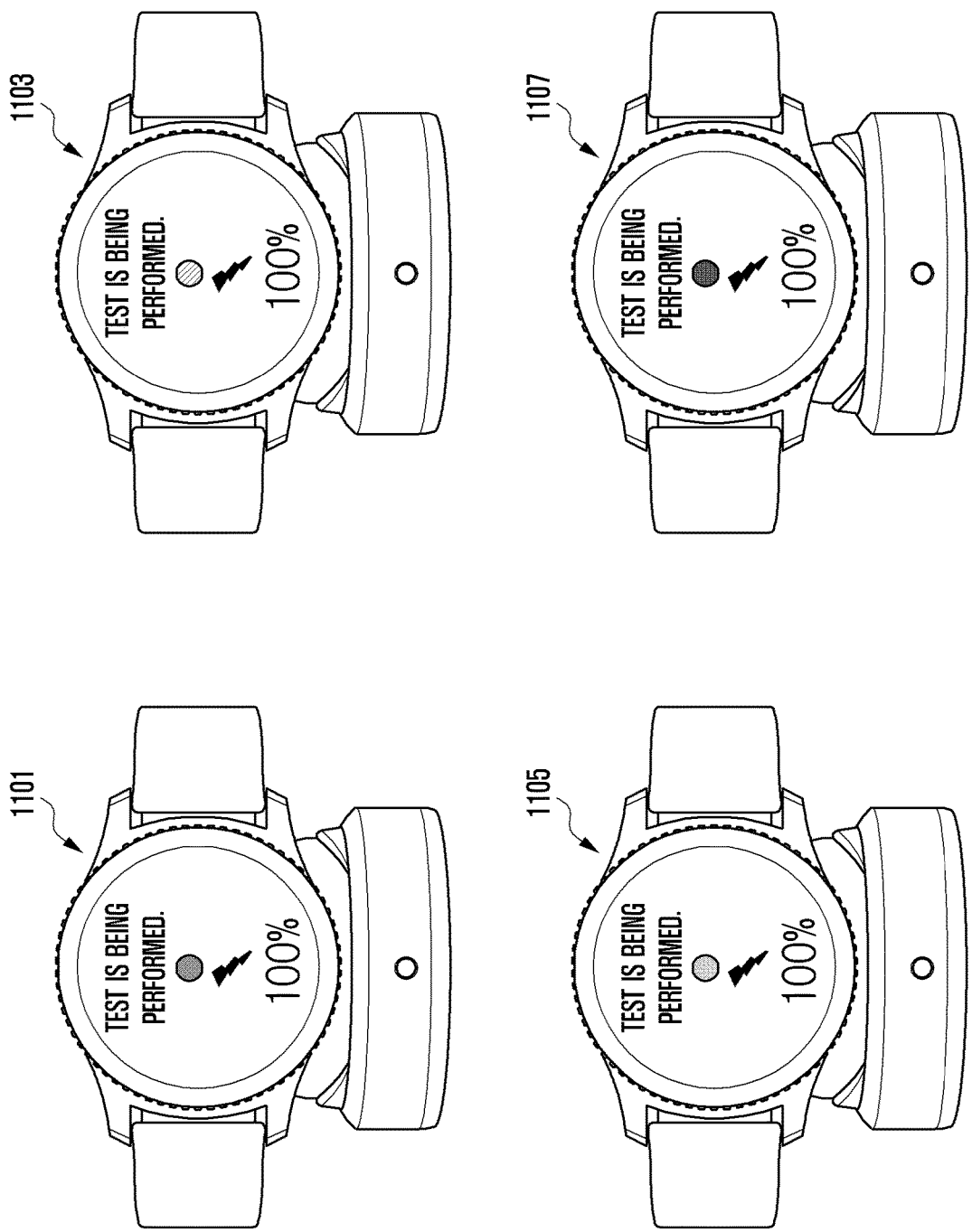
FIG. 11 is views illustrating an operation of an electronic device according to an embodiment of the disclosure.

FIG. 11 is views illustrating an operation of an electronic device according to an embodiment of the disclosure.

According to an embodiment, the electronic devices 1101, 1103, 1105, and 1107 (e.g., the electronic device 101 of FIG. 1, the electronic device 200 of FIGS. 2 and 3, the electronic device 400 of FIG. 4, and the electronic device 500 of FIG. 5) may provide information representing that a sensor (e.g., the sensor module 176 of FIG. 1, the sensor module 211 of FIG. 3, the light sensor 551 of FIG. 5, and the PPG sensors 601 and 603 of FIGS. 6A and 6B) is performing a test. For example, the electronic devices 1101, 1103, 1105, and 1107 may provide a test progress situation to the user through a user interface (e.g., implemented using display, speaker, or LED). For example, the electronic devices 1101, 1103, 1105, and 1107 may provide information about a charging progress status, an LED or a photodiode under test, or information related to a time period required for the test through the display. For example, the electronic devices 1101, 1103, 1105, and 1107 may output light of the same color as that of the LED under test. For example, in each case of 1101, 1103, 1105, and 1107, the user may recognize that the electronic device 1101, 1103, 1105, or 1107 is testing an LED or a photodiode of a particular color according to text or color displayed in the user interface.

According to an embodiment, the electronic devices 1101, 1103, 1105, and 1107 may provide information about a test progress situation together with information related to charging while the device is charging.

Figure 12:
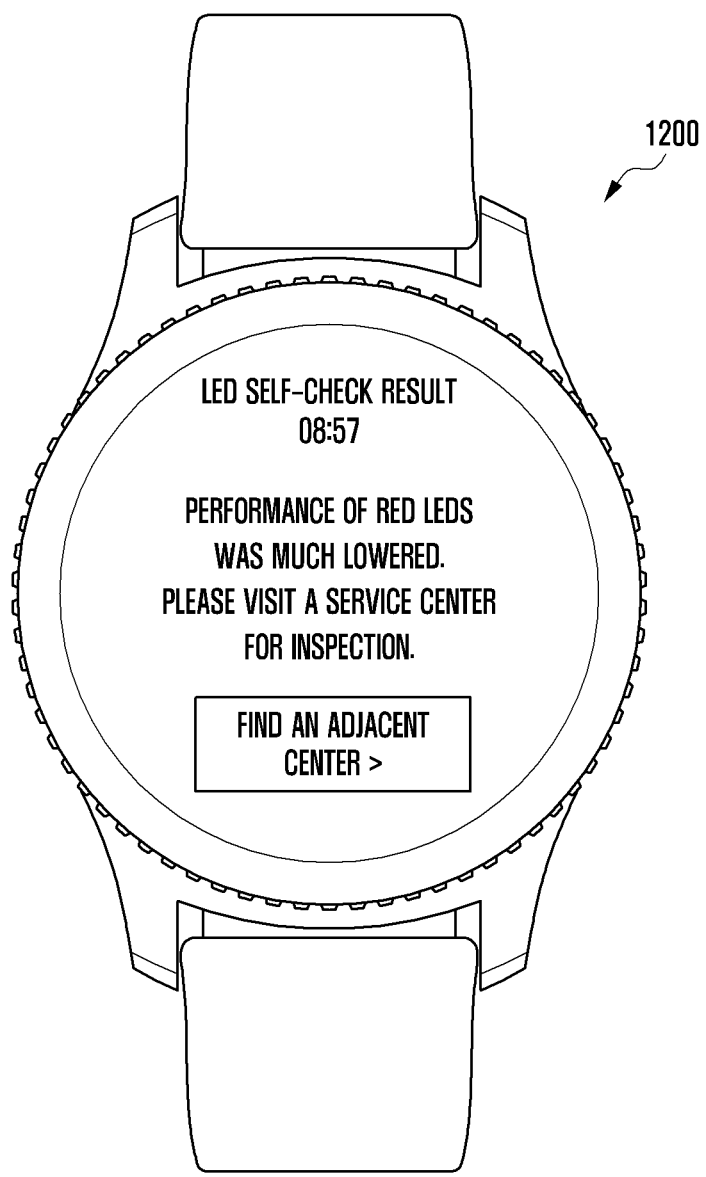
FIG. 12 is a view illustrating an operation of an electronic device according to an embodiment of the disclosure.

FIG. 12 is a view illustrating an operation of an electronic device according to an embodiment of the disclosure.

According to an embodiment of the disclosure, an electronic device 1200 (e.g., the electronic device 101 of FIG. 1, the electronic device 200 of FIGS. 2 and 3, the electronic device 400 of FIG. 4, and the electronic device 500 of FIG. 5) may provide information about a state of a PPG sensor (e.g., the sensor module 176 of FIG. 1, the sensor module 211 of FIG. 3, the light sensor 551 of FIG. 5, and the PPG sensors 601 and 603 of FIGS. 6A and 6B) through a user interface. According to one embodiment, the user interface may be implemented through a display, a speaker, or an LED.

According to an embodiment, when the state of the PPG sensor has deteriorated to the point where it cannot guarantee accuracy, the electronic device 1200 may notify the user of this. For example, when the PPG sensor of the electronic device 1200 includes one or more LEDs or one or more photodiodes, the electronic device 1200 may provide information about a severely deteriorated LED or photodiode to the user.

For example, the electronic device 1200 may provide notification that a performance of a specific and damaged device (LED or photodiode) has been lowered through the user interface and provide a notification that recommends a visit to a service center or an after-sales service. According to an embodiment, the electronic device 1200 may provide information of a service center near a current location or a service center related to user information (e.g., a home address of the user).

According to an embodiment, when the electronic device 1200 performs calibration of the PPG sensor, the electronic device 1200 may provide a result of the calibration through the user interface.

Figure 13:
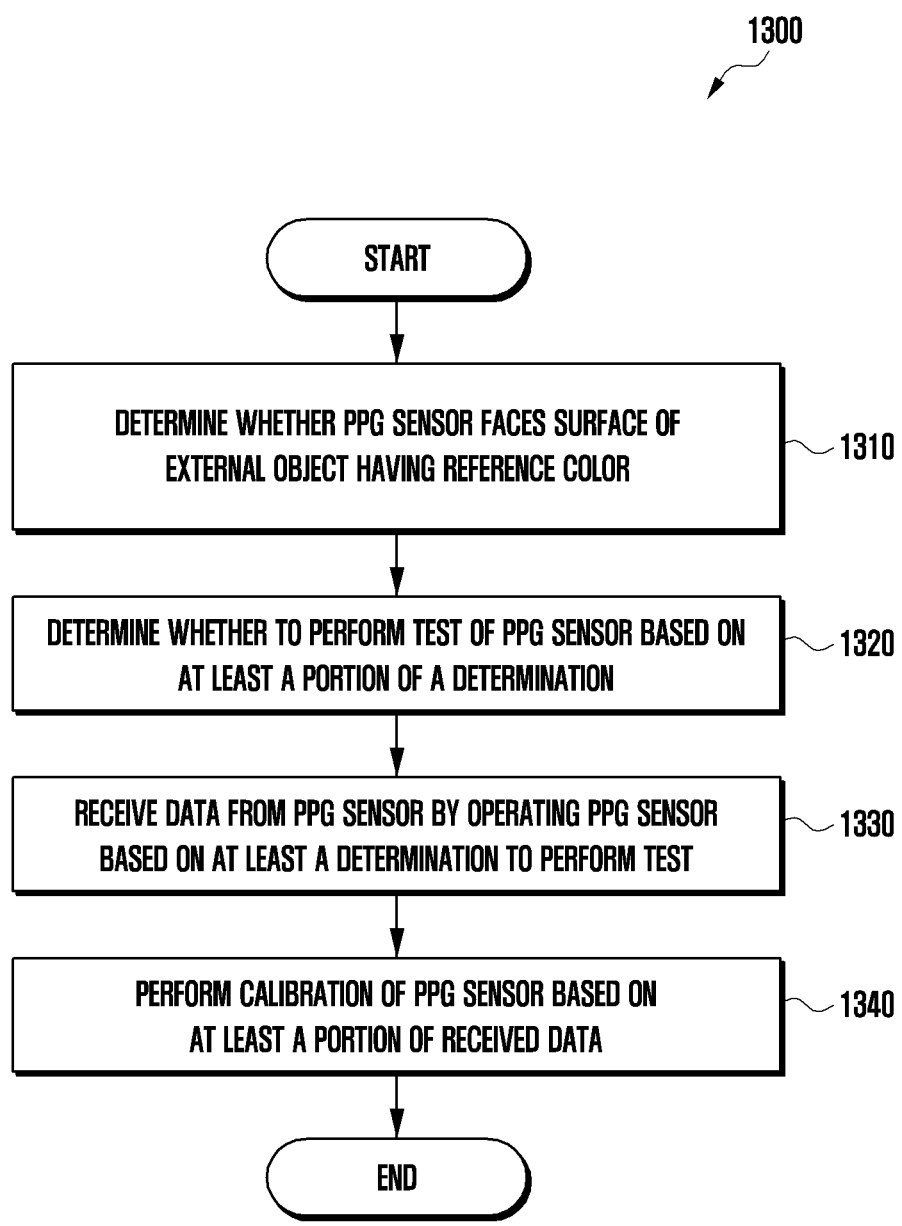
FIG. 13 is a flowchart illustrating a method of operating an electronic device according to an embodiment of the disclosure.

FIG. 13 is a flowchart 1300 illustrating a method of operating an electronic device according to an embodiment of the disclosure.

According to an embodiment, in operation 1310, an electronic device (e.g., the electronic device 101 of FIG. 1, the electronic device 200 of FIGS. 2 and 3, the electronic device 400 of FIG. 4, and the electronic device 500 of FIG. 5) may determine whether a photoplethysmogram (PPG) sensor (e.g., the sensor module 176 of FIG. 1, the sensor module 211 of FIG. 3, the light sensor 551 of FIG. 5, and the PPG sensors 601 and 603 of FIGS. 6A and 6B) is facing a surface of an external object having a reference color. According to an embodiment, the PPG sensor may include a light receiving module exposed through a portion of the housing of the electronic device and including at least one LED and at least one photodiode.

According to an embodiment, the electronic device may output light to an external object using at least one LED included in the PPG sensor. According to an embodiment, the electronic device may receive light reflected by the external object using a light receiving module (e.g., at least one photodiode) included in the PPG sensor. According to an embodiment, the electronic device may recognize reflectivity of light based on the output light and the received light and determine whether the PPG sensor is facing a surface of the external object based on the determined reflectivity. For example, reflectivity of light may vary depending on the color of the surface of the external object. When the electronic device emits light of a specific wavelength toward the external object, the amount of light received by the electronic device may vary depending on the color of the surface of the external object. According to an embodiment, the electronic device may store information about reflectivity of various colors. For example, when the electronic device emits light of a specific wavelength or a specific color to the external device, the electronic device may store information about the amount of light reflected and received from the external device, which may vary depending on the color of the external device. For example, the electronic device may compare or analyze data received from the PPG sensor with the stored information to determine whether the PPG sensor of the electronic device is facing the external object having the reference color.

According to an embodiment, the electronic device may determine whether the PPG sensor is facing a surface of the external object based on whether a battery of the electronic device is being charged. For example, when the electronic device is being charged, the electronic device may determine whether the PPG sensor is facing a surface of the external object. In another example, when the electronic device is connected to an external charger (e.g. via a charging wire) or mounted in an external charger (e.g., charging dock), the electronic device is not used by the user or is not moving. The electronic device may determine whether the PPG sensor is facing a surface of the charger having a reference color while the device is charging. For example, when the charger is black, the electronic device may determine whether the PPG sensor is facing a black surface of the charger. According to an embodiment, the electronic device may set, by a user input, the color of at least a portion of the charger in which the PPG sensor is facing to a reference color while the electronic device is being mounted on the charger.

According to an embodiment, the electronic device may determine the execution frequency of the PPG sensor. According to an embodiment, the electronic device may determine a test execution period of the PPG sensor based on the execution frequency. For example, the electronic device may determine a measurement frequency of a biometric signal of the user using the PPG sensor. The electronic device may then determine a test execution period of the PPG sensor based on the measurement frequency of the biometric signal. According to an embodiment, the electronic device may determine whether the PPG sensor is facing a surface of an external object having a reference color during the determined test execution period.

According to an embodiment, the electronic device may determine a use frequency of each of the at least one LED or at least one photodiode included in the PPG sensor based on an execution frequency. According to an embodiment, the electronic device may determine a test execution period of each of the at least one LED or at least one photodiode based on the use frequency. For example, the use frequency the LEDs or photodiodes may be different depending on type of the biometric signal that is measured by the user. For example, in order to measure heart rate, stress, and blood pressure, the electronic device may use an LED for outputting green light, in order to measure blood sugar, the electronic device may use an LED for outputting blue light or an LED for outputting infrared light, in order to measure oxygen saturation, the electronic device may use an LED for outputting red light and an LED for outputting infrared light. LEDs of a PPG sensor that are used more frequently by the electronic device may be more likely to deteriorate faster. The electronic device may determine a test execution period of each LED or photodiode so that a performance of an LED or photodiode of the PPG sensor that has a high use frequency is tested more frequently.

According to an embodiment, in operation 1320, the electronic device may determine whether to perform a test of the PPG sensor based on at least the determination result on whether the PPG sensor is facing a surface of the external object having a reference color. For example, when the PPG sensor is facing the surface, the electronic device may perform a test of the PPG sensor. Alternatively, when the PPG sensor is not facing the surface, the test of the PPG sensor may not be performed or the electronic device may end performance of the test of the PPG sensor.

According to an embodiment, the electronic device may determine whether to perform the test based on at least a portion of data from a motion sensor of the electronic device. For example, the electronic device may recognize whether the electronic device is moving based on at least a portion of data from the motion sensor. When the electronic device is moving, the electronic device may be in use or it may be difficult to accurately test a state of the PPG sensor. On the other hand, when there is no movement in the electronic device for a predetermined time period or more based on data from the motion sensor, the electronic device may start the test of the PPG sensor. For example, the electronic device may perform the test of the PPG sensor while there is no movement of the electronic device based on data from the motion sensor. Alternatively, when movement of the electronic device is detected based on data from the motion sensor, the electronic device may end the test of the PPG sensor.

According to an embodiment, in operation 1330, the electronic device may operate the PPG sensor to receive data from light receiving module (e.g., photodiode) based on at least a determination to whether to perform the test.

According to an embodiment, the electronic device may emit light through at least one LED of the PPG sensor and measure the amount of light received through at least one photodiode included in the PPG sensor. For example, when the PPG sensor includes a plurality of photodiodes, the electronic device may operate each of the plurality of photodiodes sequentially and individually to measure the amount of received light. According to an embodiment, when the electronic device emits light of a specific wavelength toward a surface of the external object of a reference color, the electronic device may store reference information about the amount of received light through a specific photodiode as, for example, a specification of that photodiode. For example, the electronic device may emit light of a specific wavelength using the LED of the PPG sensor and then compare the amount of light received through at least one photodiode included in the PPG sensor with the stored reference information to determine a state of the at least one photodiode. For example, when the PPG sensor includes a plurality of photodiodes, the electronic device may measure the amount of light received sequentially from the plurality of photodiodes and compare amounts of light received through each of the plurality of photodiodes to determine a state of each of the plurality of photodiodes.

According to an embodiment, the electronic device may emit light through each of the LEDs of the PPG sensor and measure the amount of light received through a light receiving module (e.g., photodiode) included in the PPG sensor. For example, when the PPG sensor includes a plurality of LEDs, the electronic device may emit light sequentially and independently through each of the plurality of LEDs and measure the amount of received light using at least one photodiode included in the PPG sensor. According to an embodiment, when the electronic device emits light of a specific wavelength toward a surface of an external object of a reference color, the electronic device may store reference information about the amount of light received through a specific photodiode as specification information for that LED. For example, the electronic device may emit light through each of at least one LED of the PPG sensor and then compare the amount of light received through at least one photodiode included in the PPG sensor with the stored reference information to determine a state of each of at least one LED.

According to different embodiments, the electronic device may first perform a test of each of the photodiodes included in the PPG sensor and perform a test of each of the LEDs included in the PPG sensor or first perform a test of each LED and then perform a test of each photodiode. According to an embodiment, the electronic device may compare data corresponding to the LEDs or photodiodes included in the PPG sensor to each other to test performance of the plurality of LEDs or photodiodes.

According to an embodiment, in operation 1340, the electronic device may perform a calibration of the PPG sensor based on at least a portion of data received from the PPG sensor. For example, the electronic device may determine whether at least one LED or at least one photodiode included in the PPG sensor is abnormal and perform a calibration of the LED or the photodiode having abnormality. As such, the electronic device may increase the accuracy of the PPG sensor through a calibration.

According to an embodiment, the electronic device may change a resistance value or a gain value set for at least one photodiode included in the PPG sensor as at least a portion of the calibration. For example, the electronic device may convert light received through the photodiode to an electrical signal (e.g., current). In an example of calibration, the electronic device may change the resistance value or the gain value set for the current converted through the photodiode. For example, when light is emitted through a PPG sensor (e.g., LED) of the electronic device, the amount of light received through the PPG sensor (e.g., light receiving module or photodiode) may increase according to the intensity of the emitted light. The electronic device may change the resistance value or the gain value set for a partial current segment or the entire current segment in which deterioration occurs to increase measurement accuracy of the PPG sensor.

According to an embodiment, the electronic device may provide a calibration result through a user interface. According to one embodiment, the user interface may be implemented through a display, a speaker, or an LED. For example, the electronic device may provide information about a charging progress situation, an LED under test, and a photodiode or information related to a time required for a test through a display. According to an embodiment, in a charging state, the electronic device may provide information about a test progress situation together with information related to charging.

According to an embodiment, the electronic device may provide information about a state of the PPG sensor through the user interface. According to an embodiment, when a state of the PPG sensor is at a level that cannot guarantee accuracy, the electronic device may notify the user of this. For example, when the PPG sensor of the electronic device includes one or more LEDs or one or more photodiodes, the electronic device may provide information to the user about an LED or a photodiodes severely deteriorated. For example, the electronic device may provide notification through the user interface (e.g., display) that a performance of a specific element (LED or photodiode) having severe damage has been lowered and provide a notification that recommends a visit to a service center or an after-sales service. According to an embodiment, the electronic device may provide information of a service center close to a current location or a service center related to user information (e.g., a home address of the user).

A method of operating an electronic device (e.g., the electronic device 101 of FIG. 1, the electronic device 200 of FIGS. 2 and 3, the electronic device 400 of FIG. 4, and the electronic device 500 of FIG. 5) according to an embodiment of the disclosure may include determining whether a photoplethysmogram (PPG) sensor (e.g., the sensor module 176 of FIG. 1, the sensor module 211 of FIG. 3, the light sensor 551 of FIG. 5, and the PPG sensors 601 and 603 of FIGS. 6A and 6B) including a light receiving module exposed through a portion of a housing (e.g., the housing 210 of FIGS. 2 and 3) of the electronic device, at least one LED, and at least one photodiode is facing a surface of an external object having a reference color; determining whether to perform a test of the PPG sensor based on whether the PPG sensor is facing the surface; receiving data from the PPG sensor by operating the PPG sensor in response to determining to perform the test; and performing calibration of the PPG sensor based on at least a portion of the received data.

According to one embodiment, the PPG sensor is determined to face the surface of the external object based on whether the battery (e.g., the battery 189 of FIG. 1, the battery 470 of FIG. 4, and the charging module 510 of FIG. 5) of the electronic device is being charged.

According to an embodiment, determining whether to perform the test of the PPG sensor may be based on at least a portion of data from a motion sensor (e.g., the sensor module 176 of FIG. 1, the sensor module 211 of FIG. 3, and the motion sensor 553 of FIG. 5) of the electronic device.

According to an embodiment, the method may further include providing a result of the calibration through a user interface (e.g., the display device 160, the audio output device 155, or the interface 177 of FIG. 1, the audio modules 205 and 208 of FIGS. 2 and 3, the display 220 of FIG. 4, and the display device 540 of FIG. 5) of the electronic device.

According to an embodiment, the user interface may be implemented through at least one of a display (e.g., the display device 160 of FIG. 1, the display 220 of FIG. 4, and the display device 540 of FIG. 5), a speaker (e.g., the audio output device 155 of FIG. 1, the audio modules 205 and 208 of FIGS. 2 and 3), or a light emitting diode (LED).

According to an embodiment, the method may further include providing information about a state of the PPG sensor through the user interface.

According to one embodiment, determining whether a photoplethysmogram (PPG) sensor faces a surface of an external object may include outputting light to the external object through the at least one LED; receiving light reflected by the external object through the light receiving module; determining reflectivity of light based on the output light and the received light; and determining whether the PPG sensor is facing the surface of the external object having the reference color based on the reflectivity of light.

According to one embodiment, the method may further include determining an execution frequency of a function of the PPG sensor; and determining a test execution period of the PPG sensor based on the execution frequency.

According to an embodiment, determining the first test execution period of the PPG sensor may include determining a use frequency of at least one LED or at least one photodiode included in the PPG sensor based on the execution frequency; and determining a second test execution period or a test execution order of the at least one LED or at least one photodiode based on the use frequency.

According to an embodiment, performing of the calibration may include changing a resistance value or a gain value set for the at least one photodiode.

Electronic devices according to certain embodiments disclosed in this document may be various types of devices. The electronic device may include, for example, a mobile communication device (e.g., smartphone), computer device, mobile multimedia device, mobile medical device, camera, wearable device, or home appliance device. Electronic devices according to embodiments of this document are not limited to the above-described devices.

It should be understood that certain embodiments of this document and terms used in the embodiments do not limit technical characteristics described in this document to a specific embodiment and include various changes, equivalents, or replacements of a corresponding embodiment. The same reference numbers are used throughout the drawings to refer to the same or like parts. A singular form of a noun corresponding to an item may include one or more of the items, unless the context clearly indicates otherwise. In this document, each of phrases such as "A or B", "at least one of A and B", "at least one of A or B," "A, B or C," "at least one of A, B and C," and "at least one of A, B, or C," may include any one of items listed together with the corresponding phrase of the phrases or any possible combination thereof. Terms such as "first" or "second" may simply be used for distinguishing a component from other corresponding components, and does not limit the components in other aspects (e.g., importance or order). When any (e.g., first) component is referred to as "coupled" or "connected" to another (e.g., second) component, with or without the term "functionally" or "communicably", it means that any component may be connected directly to the other component (e.g., by a wire means), by a wireless means, or through a third component.

The term "module" used in this document may include a unit implemented into hardware, software, or firmware and may be interchangeably used with a term such as logic, logic block, component, or circuit. The "module" may be an integrally configured component or a minimum unit that performs at least one function or a portion thereof. For example, according to one embodiment, the module may be implemented in the form of an application-specific integrated circuit (ASIC).

Various embodiments of this document may be implemented as software (e.g., the program 140) including one or more instructions stored at a storage medium (e.g., the internal memory 136 or the external memory 138) that may be read by a machine (e.g., the electronic device 101). For example, the processor (e.g., the processor 120) of the device (e.g., the electronic device 101) may call and execute at least one command of one or more stored instructions from the storage medium. This enables the device to be operated to perform at least one function according to the at least one called command. The one or more instructions may include a code generated by a compiler or a code executable by an interpreter. The device readable storage medium may be provided in the form of a non-transitory storage medium. Here, "non-transitory" means only that the storage medium is a tangible device and does not include a signal (e.g., electromagnetic wave), which does not distinguish a case in which data are stored semi-permanently at the storage medium and a case in which data are temporarily stored.

According to an embodiment, a method according to certain embodiments disclosed in this document may be included and provided in a computer program product. The computer program product may be traded as a product between a seller and a buyer. The computer program product may be distributed in the form of a device readable storage medium (e.g., compact disc read only memory (CD-ROM)) or through an application store (e.g., Play Store™) or may be distributed (e.g., downloaded or uploaded) directly or online between two user devices (e.g., smartphones). In a case of online distribution, at least a portion of the computer program product may be at least temporarily stored or temporarily generated in a device readable storage medium such as a server of a manufacturer, a server of an application store, or a memory of a relay server.

According to certain embodiments, each component (e.g., module or program) of the above-described components may include a singular entity or a plurality of entities. According to certain embodiments, one or more of the aforementioned components or operations may be omitted, or one or more other components or operations may be added. Alternatively or additionally, a plurality of components (e.g., module or program) may be integrated into one component. In this case, the integrated component may perform one or more functions of each of the plurality of components to be the same as or similar to that performed by the corresponding component of the plurality of components before the integration. According to certain embodiments, operations performed by a module, a program, or another component may be sequentially, in parallel, repeatedly, or heuristically executed, at least one of the operations may be executed in a different order or omitted, or another operation may be added.

An electronic device and a method of operating the same according to certain embodiments of the disclosure can notify a user of a state of a sensor (e.g., photoplethysmogram (PPG) sensor) included therein.

An electronic device and a method of operating the same according to certain embodiments of the disclosure can perform calibration of a PPG sensor included therein to calibrate accuracy of the PPG sensor.

Certain of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

While the disclosure has been shown in particular and described with reference to embodiments thereof, it will be understood by those skilled in the art that various changes in form and details may be made therein without departing from the scope of the subject matter as defined by the appended claims.

What is claimed is:

1. An electronic device, comprising:
a housing;
a rechargeable battery;
a user interface;

a photoplethysmogram (PPG) sensor including a light receiving module exposed through a portion of the housing, at least one light emitting diode (LED), and at least one photodiode;

a processor operatively connected to the battery, the user interface, and the PPG sensor; and a memory operatively connected to the processor, wherein the memory stores instructions that, when executed, cause the processor to:

determine whether the PPG sensor is facing a surface of an external object having a reference color based on whether the battery is charged, determine whether to perform a test of the PPG sensor based on whether the PPG sensor is facing the surface, receive data from the PPG sensor by operating the PPG sensor in response to determining to perform the test, and perform a calibration of the PPG sensor based on at least a portion of the received data.

2. The electronic device of claim 1, further comprising a motion sensor, wherein the instructions further cause the processor to determine whether to perform the test based on at least a portion of data from the motion sensor.

3. The electronic device of claim 1, wherein the instructions further cause the processor to provide a result of the calibration through the user interface.

4. The electronic device of claim 3, wherein the user interface is implemented through a display, a speaker, and/or an LED.

5. The electronic device of claim 4, wherein the instructions further cause the processor to provide information about a state of the PPG sensor through the user interface.

6. The electronic device of claim 1, wherein the instructions further cause the processor to:

output light to the external object using the at least one LED, receive light reflected by the external object using the light receiving module, determine reflectivity of light based on the output light and the received light, and determine whether the PPG sensor is facing the surface of the external object having the reference color based on the reflectivity of light.

7. The electronic device of claim 1, wherein the instructions further cause the processor to:

determine an execution frequency of a function of the PPG sensor, and determine a first test execution period of the PPG sensor based on the execution frequency.

8. The electronic device of claim 7, wherein the instructions further cause the processor to:

determine a use frequency of the at least one LED or the at least one photodiode included in the PPG sensor based on the execution frequency, and determine a second test execution period or a test execution order of the at least one LED or the at least one photodiode based on the use frequency.

9. The electronic device of claim 1, wherein the instructions further cause the processor to change a resistance value or a gain value set for the at least one photodiode as at least a portion of the calibration.

10. A method of operating an electronic device, the method comprising:

determining whether a photoplethysmogram (PPG) sensor including a light receiving module exposed through a portion of a housing of the electronic device, at least one light emitting diode (LED), and at least one photodiode is facing a surface of an external object having a reference color based on whether the battery is charged;

determining whether to perform a test of the PPG sensor based on whether the PPG sensor is facing the surface;

receiving data from the PPG sensor by operating the PPG sensor in response to determining to perform the test; and performing a calibration of the PPG sensor based on at least a portion of the received data.

11. The method of claim 10, wherein whether to perform the test is determined based on at least a portion of data from a motion sensor of the electronic device.

12. The method of claim 10, further comprising providing a result of the calibration through a user interface of the electronic device.

13. The method of claim 12, wherein the user interface is implemented through a display, a speaker, and/or an LED.

14. The method of claim 13, further comprising providing information about a state of the PPG sensor through the user interface.

15. The method of claim 10, wherein determining whether a photoplethysmogram (PPG) sensor faces a surface comprises:

outputting light to the external object through the at least one LED;

receiving light reflected by the external object through the light receiving module;

determining reflectivity of light based on the output light and the received light; and determining whether the PPG sensor is facing the surface of the external object having the reference color based on the reflectivity of light.

16. The method of claim 10, further comprising:

determining an execution frequency of a function of the PPG sensor; and determining a first test execution period of the PPG sensor based on the execution frequency.

17. The method of claim 16, wherein determining the first test execution period of the PPG sensor further comprises:

determining a use frequency of the at least one LED or the at least one photodiode included in the PPG sensor based on the execution frequency; and determining a second test execution period or a test execution order of the at least one LED or the at least one photodiode based on the use frequency.

18. The method of claim 10, wherein performing the calibration of the PPG sensor further comprises changing a resistance value or a gain value set for the at least one photodiode.

* * * * *